(12) United States Patent
Bar-Or

(10) Patent No.: US 9,522,893 B2
(45) Date of Patent: Dec. 20, 2016

(54) THERAPEUTIC METHODS AND COMPOUNDS

(71) Applicant: Ampio Pharmaceuticals, Inc., Englewood, CO (US)

(72) Inventor: David Bar-Or, Englewood, CO (US)

(73) Assignee: Ampio Pharmaceuticals, Inc., Englewood, CO (US)

( * ) Notice: Subject to any disclaimer, the term of this patent is extended or adjusted under 35 U.S.C. 154(b) by 0 days.

(21) Appl. No.: 14/470,487

(22) Filed: Aug. 27, 2014

(65) Prior Publication Data

US 2015/0051224 A1 Feb. 19, 2015

Related U.S. Application Data

(62) Division of application No. 13/403,419, filed on Feb. 23, 2012, now Pat. No. 8,871,772, which is a division of application No. 12/472,738, filed on May 27, 2009, now Pat. No. 8,217,047.

(60) Provisional application No. 61/056,379, filed on May 27, 2008.

(51) Int. Cl.
*C07D 241/08* (2006.01)

(52) U.S. Cl.
CPC ................................... *C07D 241/08* (2013.01)

(58) Field of Classification Search
CPC .................................................... C07D 241/08
See application file for complete search history.

(56) References Cited

U.S. PATENT DOCUMENTS

| | | |
|---|---|---|
| 2,507,631 A | 5/1950 | Hartmann et al. |
| 2,957,880 A | 10/1960 | Rometsch et al. |
| 3,763,091 A | 10/1973 | Crescenzi et al. |
| 3,772,265 A | 11/1973 | Isowa et al. |
| 3,928,330 A | 12/1975 | Ramey et al. |
| 3,941,790 A | 3/1976 | Creighton |
| 3,976,773 A | 8/1976 | Curran |
| 4,006,261 A | 2/1977 | Pickenhagen et al. |
| 4,088,649 A | 5/1978 | Smith et al. |
| 4,205,057 A | 5/1980 | Whitaker |
| 4,289,759 A | 9/1981 | Heavner et al. |
| 4,312,987 A | 1/1982 | Beck |
| 4,331,595 A | 5/1982 | Heavner et al. |
| 4,661,500 A | 4/1987 | Rozencwaig |
| 4,694,061 A | 9/1987 | Pfeifer |
| 4,694,081 A | 9/1987 | Miller et al. |
| 4,771,056 A | 9/1988 | Rozencwaig |
| 4,806,538 A | 2/1989 | Shimazaki et al. |
| 4,886,796 A | 12/1989 | Eichner et al. |
| 4,940,709 A | 7/1990 | Shimazaki et al. |
| 4,992,552 A | 2/1991 | Hubbs et al. |
| 5,047,401 A | 9/1991 | Lipsky et al. |
| 5,144,073 A | 9/1992 | Hubbs |
| 5,238,938 A | 8/1993 | Tone et al. |
| 5,352,461 A | 10/1994 | Feldstein et al. |
| 5,358,938 A | 10/1994 | Cai et al. |
| 5,358,953 A | 10/1994 | Alker et al. |
| 5,407,926 A | 4/1995 | Clark |
| 5,418,218 A | 5/1995 | Wilber |
| 5,434,151 A | 7/1995 | Cai et al. |
| 5,463,083 A | 10/1995 | Biftu et al. |
| 5,503,852 A | 4/1996 | Steiner et al. |
| 5,512,544 A | 4/1996 | Wallach et al. |
| 5,538,993 A | 7/1996 | Mechoulam et al. |
| 5,543,402 A | 8/1996 | Bosies et al. |
| 5,543,503 A | 8/1996 | Chuntharapai et al. |
| 5,545,404 A | 8/1996 | Page |
| 5,550,132 A | 8/1996 | Benson et al. |
| 5,561,115 A | 10/1996 | Tenold |
| 5,578,323 A | 11/1996 | Milstein et al. |
| 5,589,501 A | 12/1996 | Carrera et al. |
| 5,648,486 A | 7/1997 | Cai et al. |
| 5,658,955 A | 8/1997 | Hitzig |
| 5,665,714 A | 9/1997 | Paltauf et al. |
| 5,693,338 A | 12/1997 | Milstein |
| 5,700,804 A | 12/1997 | Collins et al. |
| 5,703,093 A | 12/1997 | Cai et al. |

(Continued)

FOREIGN PATENT DOCUMENTS

| | | |
|---|---|---|
| CS | 254868 | 6/1987 |
| CZ | 2827.94 | 4/1996 |

(Continued)

OTHER PUBLICATIONS

Lindsley et. al., Bioorganic and Medicinal Chemistry Letters, 2005, Elsevier, vol. 15, pp. 761-764.*

Harada et al., "Essential involvement of interleukin-8 (IL-8) in acute inflammation," Journal of Leukocyte Biology, 1994, vol. 56, Iss. 5, pp. 559-564.

Lupia et al., "Role of tumor necrosis factor-α and platelet-activating factor in neoangiogenesis induced by synovial fluids of patients with rheumatoid arthritis," European Journal of Immunology, 1996, vol. 26, Iss. 8, pp. 1690-1694.

(Continued)

*Primary Examiner* — Sarah Pihonak

(74) *Attorney, Agent, or Firm* — Sheridan Ross P.C.

(57) ABSTRACT

The invention provides diketopiperazines of formula I. The invention also provides pharmaceutical compositions comprising the diketopiperazines, or pharmaceutically-acceptable salts or prodrugs thereof, as the active ingredient. The invention further provides therapeutic treatments that utilize the diketopiperazines of formula I, including inhibition of a proliferative disease or condition, inhibition of angiogenesis, treatment of an angiogenic disease or condition, treatment of cancer and precancerous conditions, treatment of a fibrotic disorder, treatment of a viral infection, treatment of an Akt-mediated disease or condition, inhibition of the production, release or both of matrix metalloproteinase-9, and inhibition of Akt activation.

2 Claims, 1 Drawing Sheet

(56) References Cited

U.S. PATENT DOCUMENTS

| | | |
|---|---|---|
| 5,741,809 A | 4/1998 | Biftu et al. |
| 5,750,530 A | 5/1998 | Bryans et al. |
| 5,750,565 A | 5/1998 | Cai et al. |
| 5,776,892 A | 7/1998 | Counts et al. |
| 5,780,503 A | 7/1998 | Biftu et al. |
| 5,792,776 A | 8/1998 | Biftu et al. |
| 5,811,241 A | 9/1998 | Goodfellow et al. |
| 5,817,751 A | 10/1998 | Szardenings et al. |
| 5,834,032 A | 11/1998 | Song |
| 5,843,950 A | 12/1998 | Tasaka et al. |
| 5,856,323 A | 1/1999 | Cai et al. |
| 5,859,249 A | 1/1999 | Seido et al. |
| 5,877,174 A | 3/1999 | Ono et al. |
| 5,883,227 A | 3/1999 | Kline et al. |
| 5,886,152 A | 3/1999 | Nakatani et al. |
| 5,902,812 A | 5/1999 | Brocchini et al. |
| 5,908,850 A | 6/1999 | Zeitlin et al. |
| 5,919,785 A | 7/1999 | Dinsmore et al. |
| 5,932,112 A | 8/1999 | Browning, Jr. |
| 5,932,579 A | 8/1999 | Campbell et al. |
| 5,976,569 A | 11/1999 | Milstein |
| 5,985,581 A | 11/1999 | Nixon et al. |
| 5,990,112 A | 11/1999 | Campbell et al. |
| 6,025,502 A | 2/2000 | Winklter et al. |
| 6,034,057 A | 3/2000 | Dutta |
| 6,034,221 A | 3/2000 | Berezenko et al. |
| 6,060,452 A | 5/2000 | Green et al. |
| 6,060,463 A | 5/2000 | Freeman |
| 6,090,780 A | 7/2000 | Prasad |
| 6,096,737 A | 8/2000 | Loder |
| 6,099,856 A | 8/2000 | Milstein et al. |
| 6,107,050 A | 8/2000 | Alkon et al. |
| 6,127,385 A | 10/2000 | Midha et al. |
| 6,180,616 B1 | 1/2001 | Fukunaga |
| 6,210,705 B1 | 4/2001 | Mantelle et al. |
| 6,222,029 B1 | 4/2001 | Edwards et al. |
| 6,248,363 B1 | 6/2001 | Patel et al. |
| 6,262,119 B1 | 7/2001 | Ferrante et al. |
| 6,265,535 B1 | 7/2001 | Greene et al. |
| 6,331,318 B1 | 12/2001 | Milstein et al. |
| 6,358,957 B1 | 3/2002 | Fukumoto et al. |
| 6,395,752 B1 | 5/2002 | Midha et al. |
| 6,395,774 B1 | 5/2002 | Milstein |
| 6,441,172 B1 | 8/2002 | Nefzi et al. |
| 6,461,875 B1 | 10/2002 | Bar-Or et al. |
| 6,475,743 B1 | 11/2002 | Bar-Or et al. |
| 6,486,177 B2 | 11/2002 | Zeldis et al. |
| 6,492,179 B1 | 12/2002 | Bar-Or et al. |
| 6,531,505 B2 | 3/2003 | Xu et al. |
| 6,541,224 B2 | 4/2003 | Yu et al. |
| 6,555,543 B2 | 4/2003 | Bar-Or et al. |
| 6,635,649 B2 | 10/2003 | Teng et al. |
| 6,677,473 B1 | 1/2004 | Madison et al. |
| 6,689,765 B2 | 2/2004 | Baroudy et al. |
| 6,815,214 B2 | 11/2004 | Boyce et al. |
| 6,930,112 B2 | 8/2005 | Weaver et al. |
| 6,967,202 B2 | 11/2005 | Rao et al. |
| 7,026,322 B2 | 4/2006 | Hayashi et al. |
| 7,175,844 B2 | 2/2007 | King |
| 7,267,949 B2 | 9/2007 | Richards et al. |
| 7,276,534 B2 | 10/2007 | Milstein |
| 7,288,545 B2 | 10/2007 | Teng et al. |
| 7,332,153 B2 | 2/2008 | Bhatia et al. |
| 7,378,403 B2 | 5/2008 | Kozikowski et al. |
| 7,575,929 B2 | 8/2009 | Bar-Or et al. |
| 7,732,403 B2 | 6/2010 | Bar-Or et al. |
| 7,919,497 B2 | 4/2011 | Palladino et al. |
| 8,030,488 B2 | 10/2011 | Sviridov et al. |
| 8,067,425 B2 | 11/2011 | Brimble et al. |
| 8,183,209 B2 | 5/2012 | Bar-Or et al. |
| 8,198,407 B1 | 6/2012 | Burton et al. |
| 8,217,047 B2 | 7/2012 | Bar-Or |
| 8,268,830 B2 | 9/2012 | Bar-Or et al. |
| 8,314,106 B2 | 11/2012 | Kraft |
| 8,324,167 B2 | 12/2012 | Bar-Or et al. |
| 8,383,124 B2 | 2/2013 | Zheng |
| 8,440,696 B2 | 5/2013 | Bar-Or et al. |
| 8,455,517 B2 | 6/2013 | Bar-Or et al. |
| 8,507,496 B2 | 8/2013 | Bar-Or |
| 8,513,196 B2 | 8/2013 | Bar-Or et al. |
| 8,551,953 B2 | 10/2013 | Bar-Or et al. |
| 8,841,307 B2 | 9/2014 | Bar-Or et al. |
| 8,871,772 B2 | 10/2014 | Bar-Or |
| 2002/0132793 A1 | 9/2002 | Epstein et al. |
| 2003/0119750 A1 | 6/2003 | Demuth et al. |
| 2003/0153575 A1 | 8/2003 | Orme et al. |
| 2003/0157030 A1 | 8/2003 | Davis et al. |
| 2003/0187226 A1 | 10/2003 | Goodey et al. |
| 2003/0203915 A1 | 10/2003 | Fang et al. |
| 2004/0024180 A1 | 2/2004 | Drauz et al. |
| 2004/0038865 A1 | 2/2004 | Gelber et al. |
| 2004/0063654 A1 | 4/2004 | Davis et al. |
| 2005/0096323 A1 | 5/2005 | Cheng et al. |
| 2005/0101582 A1 | 5/2005 | Lyons et al. |
| 2005/0119177 A1* | 6/2005 | Bar-Or ............... A61K 31/495 424/185.1 |
| 2005/0192290 A1 | 9/2005 | Melamed |
| 2005/0249681 A1 | 11/2005 | Heidenfelder et al. |
| 2007/0060508 A1 | 3/2007 | Haberl et al. |
| 2007/0197511 A1 | 8/2007 | Brimble et al. |
| 2007/0208087 A1 | 9/2007 | Sanders et al. |
| 2008/0009507 A1 | 1/2008 | Cosford et al. |
| 2008/0017576 A1 | 1/2008 | Belfort et al. |
| 2008/0260838 A1 | 10/2008 | Hokenson et al. |
| 2009/0038416 A1 | 2/2009 | Bonner |
| 2010/0042206 A1 | 2/2010 | Yadav et al. |
| 2010/0120056 A1 | 5/2010 | Bar-Or et al. |
| 2010/0144611 A1 | 6/2010 | Bar-Or et al. |
| 2010/0190696 A1 | 7/2010 | Bar-Or et al. |
| 2012/0058934 A1 | 3/2012 | Bar-Or |
| 2012/0094918 A1 | 4/2012 | Bar-Or et al. |
| 2012/0101129 A1 | 4/2012 | Bar-Or et al. |
| 2012/0220530 A1 | 8/2012 | Plumridge et al. |
| 2013/0065839 A1 | 3/2013 | Bar-Or et al. |
| 2013/0072684 A1 | 3/2013 | Bar-Or et al. |
| 2013/0079284 A1 | 3/2013 | Bar-Or et al. |
| 2013/0090292 A1 | 4/2013 | Bar-Or et al. |
| 2013/0303463 A1 | 11/2013 | Bar-Or |
| 2013/0345238 A1 | 12/2013 | Bar-Or et al. |
| 2014/0256642 A1 | 9/2014 | Bar-Or et al. |
| 2014/0286913 A1 | 9/2014 | Bar-Or et al. |
| 2014/0294738 A1 | 10/2014 | Bar-Or |
| 2014/0302114 A1 | 10/2014 | Bar-Or |
| 2015/0051223 A1 | 2/2015 | Bar-Or et al. |
| 2015/0352175 A1 | 12/2015 | Bar-Or et al. |
| 2015/0366932 A1 | 12/2015 | Bar-Or |
| 2016/0015705 A1 | 1/2016 | Bar-Or et al. |
| 2016/0045493 A1 | 2/2016 | Bar-Or |

FOREIGN PATENT DOCUMENTS

| | | |
|---|---|---|
| CZ | 280726 | 4/1996 |
| CZ | 2000-2680 | 7/2000 |
| CZ | 2000-2681 | 7/2000 |
| DE | 19937721 | 2/2001 |
| EP | 0043219 | 1/1982 |
| EP | 0214557 | 3/1987 |
| EP | 0216746 | 4/1987 |
| EP | 0220958 | 5/1987 |
| EP | 0493812 | 7/1992 |
| EP | 0557388 | 9/1993 |
| EP | 0610943 | 8/1994 |
| EP | 0655060 | 5/1995 |
| EP | 0835660 | 4/1998 |
| EP | 0939124 | 9/1999 |
| EP | 1445323 | 8/2004 |
| FR | 2717484 | 9/1995 |
| GB | 851972 | 10/1960 |
| GB | 2263109 | 7/1993 |
| GB | 2372740 | 9/2002 |
| JP | S52-25019 | 2/1977 |
| JP | 59-73574 | 4/1984 |
| JP | 61-112060 | 5/1986 |
| JP | 62-036331 | 2/1987 |

(56) References Cited

FOREIGN PATENT DOCUMENTS

| | | |
|---|---|---|
| JP | 63-290868 | 11/1988 |
| JP | 01-013075 | 1/1989 |
| JP | 3176478 | 7/1991 |
| JP | 05-163148 | 6/1993 |
| JP | 07-247474 | 9/1995 |
| JP | 08-277203 | 10/1996 |
| JP | 10-226615 | 8/1998 |
| JP | 10-245315 | 9/1998 |
| JP | 11-504509 | 4/1999 |
| JP | 2000-327575 | 11/2000 |
| JP | 2001-055340 | 2/2001 |
| JP | 2002-527753 | 8/2002 |
| JP | 2008-505084 | 2/2008 |
| JP | 2009-508658 | 3/2009 |
| JP | 2010-508971 | 3/2010 |
| JP | 2011-507609 | 3/2011 |
| NZ | 218088 | 1/1989 |
| NZ | 335544 | 8/2001 |
| RU | 2112242 | 5/1998 |
| RU | 2125728 | 1/1999 |
| RU | 2128840 | 4/1999 |
| WO | WO 91/14378 | 10/1991 |
| WO | WO 93/08815 | 5/1993 |
| WO | WO 94/04512 | 3/1994 |
| WO | WO 94/04513 | 3/1994 |
| WO | WO 94/04537 | 3/1994 |
| WO | WO 94/20063 | 9/1994 |
| WO | WO 95/03054 | 2/1995 |
| WO | WO 95/18610 | 7/1995 |
| WO | WO 96/00212 | 1/1996 |
| WO | WO 96/00391 | 1/1996 |
| WO | WO 96/10396 | 4/1996 |
| WO | WO 96/14317 | 5/1996 |
| WO | WO 96/32478 | 10/1996 |
| WO | WO 97/12625 | 4/1997 |
| WO | WO 97/36888 | 10/1997 |
| WO | WO 97/38011 | 10/1997 |
| WO | WO 97/48685 | 12/1997 |
| WO | WO 98/09968 | 3/1998 |
| WO | WO 98/40748 | 9/1998 |
| WO | WO 99/16439 | 4/1999 |
| WO | WO 99/36403 | 7/1999 |
| WO | WO 99/40931 | 8/1999 |
| WO | WO 99/49865 | 10/1999 |
| WO | WO 99/51256 | 10/1999 |
| WO | WO 99/51720 | 10/1999 |
| WO | WO 00/20454 | 4/2000 |
| WO | WO 00/20840 | 4/2000 |
| WO | WO 00/22439 | 4/2000 |
| WO | WO 00/43000 | 7/2000 |
| WO | WO 00/57187 | 9/2000 |
| WO | WO 00/59880 | 10/2000 |
| WO | WO 00/74680 | 12/2000 |
| WO | WO 01/30337 | 5/2001 |
| WO | WO 01/34586 | 5/2001 |
| WO | WO 01/64241 | 9/2001 |
| WO | WO 01/68053 | 9/2001 |
| WO | WO 01/91713 | 12/2001 |
| WO | WO 02/11676 | 2/2002 |
| WO | WO 02/12201 | 2/2002 |
| WO | WO 02/059604 | 8/2002 |
| WO | WO 02/062797 | 8/2002 |
| WO | WO 02/083667 | 10/2002 |
| WO | WO 02/089738 | 11/2002 |
| WO | WO 03/032809 | 4/2003 |
| WO | WO 03/037247 | 5/2003 |
| WO | WO 03/045395 | 6/2003 |
| WO | WO 2004/005292 | 1/2004 |
| WO | WO 2004/034060 | 4/2004 |
| WO | WO 2004/043480 | 5/2004 |
| WO | WO 2004/048345 | 6/2004 |
| WO | WO 2004/054498 | 7/2004 |
| WO | WO 2004/058289 | 7/2004 |
| WO | WO 2004/103304 | 12/2004 |
| WO | WO 2005/000203 | 1/2005 |
| WO | WO 2005/011699 | 2/2005 |
| WO | WO 2006/023943 | 3/2006 |
| WO | WO 2007/098500 | 8/2007 |
| WO | WO 2007/121411 | 10/2007 |
| WO | WO 2007/149730 | 12/2007 |
| WO | WO 2008/008357 | 1/2008 |
| WO | WO 2009/009793 | 1/2009 |
| WO | WO 2009/032651 | 3/2009 |
| WO | WO 2009/042193 | 4/2009 |
| WO | WO 2012/033789 | 3/2012 |
| WO | WO 2012/174472 | 12/2012 |

OTHER PUBLICATIONS

Shimonkevitz et al., "A Diketopiperazine Fragment of Human Serum Albumin Modulates T-Lymphocyte Cytokine Production Through Rap1," Journal of Trauma, Injury, Infection, and Critical Care, 2008, vol. 64, No. 1, pp. 35-41.
Damia et al., "Contemporary pre-clinical development of anticancer agents—What are the optimal preclinical models?" European Journal of Cancer, 2009, vol. 45, Iss. 16, pp. 2768-2781.
Ocana et al., "Preclinical development of molecular-targeted agents for cancer," Nature Reviews Clinical Oncology, 2011, vol. 8, Iss. 4, pp. 200-209.
Sharma et al.,"Cell line-based platforms to evaluate the therapeutic efficacy of candidate anticancer agents" Nature Reviews Cancer, 2010, vol. 10, Iss. 4, pp. 241-253.
Wilhelm et al., "Regorafenib (BAY 73/4506): A new oral multikinase inhibitor of angiogenic, stromal and oncogenic receptor tyrosine kinases with potent preclinical antitumor activity," International Journal of Cancer, 2011, vol. 129, Iss. 1, pp. 245-255.
Del Fresno et al. "Solid-phase synthesis of diketopiperazines, useful scaffolds for combinatorial chemistry," Tetrahedron Letters, 1998, vol. 39, Iss. 17, pp. 2639-2642.
Falorni et al. "Chiral ligands containing heteroatoms. 11. Optically active 2-hydroxymethyl piperazines as catalysts in the enantioselective addition of diethylzinc to benzaldehyde," Tetrahedron: Asymmetry, 1993, vol. 4, Iss. 11, pp. 2389-2398.
Falorni et al. "Chiral ligands containing heteroatoms. 11. Optically active 2-hydroxymethyl piperazines as catalysts in the enantioselective addition of diethylzinc to benzaldehyde," Tetrahedron: Asymmetry, 1993, vol. 4, Iss. 11, pp. 2389-2398. (Abstract and Graphic only).
Matejschuk et al., "Production of human albumin solution: a continually developing colloid," British Journal of Anaesthesia, 2000, vol. 85, Iss. 6, pp. 887-895.
Meltzer, "Efficacy and patient satisfaction with cromolyn sodium nasal solution in the treatment of seasonal allergic rhinitis: a placebo-controlled study," Clinical Therapeutics, 2002, vol. 24, Iss. 6, pp. 942-952.
Pötgens et al., "Covalent dimerization of vascular permeability factor/vascular endothelial growth factor is essential for its biological activity. Evidence from Cys to Ser mutations," The Journal of Biological Chemistry, 1994, vol. 269, Iss. 52, pp. 32879-32885.
Ziong et al., "Chemical Constituents from Phytolacca polyandra" Yunnan Zhiwu Yanjiu, 2002, vol. 24, No. 3, pp. 401-405. (English abstract).
Suguna et al., "Crystal structures of diketopiperazines containing α-aminoisobutyric acid: Cyclo(Aib-Aib) and cyclo(Aib-L-Ile)," Biopolymers, 1982, vol. 21, Iss. 9, pp. 1847-1855.
"A to Z List of Cancers: Y," National Cancer Institute, 2014 [retrieved on Jan. 13, 2014], 1 pages. Retrieved from: www.cancer.gov/cancertopics/types/alphalist/y.
"CENTRICON Centrifugal Filter Devices User Guide," Millipore Corp., Mar. 2005, 23 pages.
Cytokines and Autoimmune Diseases, edited by Kuchroo, et al., 2002, Humana Press Inc., Totowa, NJ, pp. 3-23, 389-406.
Cytokines and Autoimmune Diseases, edited by Kuchroo, et al., 2002, Humana Press Inc., Totowa, NJ, pp. 5, 11, and 391.
Database WPI Section Ch, Week 199844 Derwent Publications Ltd., London, GB; Class B03, AN 1998-515050 XP002369751 & JP 10 226615 A (Pola Chem Ind Inc) Aug. 25, 1998 (Aug. 25, 1998).

(56) References Cited

OTHER PUBLICATIONS

"Diabetic Retinopathy—What you should know," National Institutes of Health, 2003, NIH Publication No. 06-2171, 24 pages.
"Disposable PD-10 Desalting Columns," GE Healthcare Life Sciences, downloaded Nov. 1, 2011, 2 pages.
"Desalting and buffer exchange with Sephadex® G-25," Amersham Biosciences, downloaded from www.gelifesciences.com on Jan. 8, 2013, 8 pages.
"Human Albumin," Sigma downloaded from www.sigmaaldrich.com on Jan. 8, 2013, 1 page.
"InteliHealth: Multiple Sclerosis," available on the World Wide Web at www.intelihealth.com/IH/ihtIH/WSIHW000/9339/10372.html, downloaded on May 7, 2006.
Online Medical Dictionary definition of albumin, medical-dictionary.thefreedictionary.com/albumin, downloaded Nov. 1, 2011, 4 pages.
The Cytokine Handbook, edited by Thomson and Lotze, 4th edition, 2003 Academic Press, vol. I, London, UK, pp. 169, 186, 187, 467, 570, 571, 838, 839, 1189-1193, 1197-1200.
The Cytokine Handbook, edited by Thomson and Lotze, 4th edition, 2003 Academic Press, vol. II, London, UK, pp. 838-860 and 1189-1211.
The Cytokine Handbook, edited by Thomson and Lotze, 4th edition, 2003 Academic Press, vol. I, London, UK, pp. 167-199, 456-474, 567-601.
The Dictionary of Immunology, Fourth Edition, Edited by Herbert et al., 1995, pp. 51-52 and 69.
"Tryprostatin A, Aspergillus fumigates," available at www.emdbiosciences.com/Products/ProductDisplay.asp?catno=649305&, printed on Jun. 21, 2006, 1 page.
'T Hart et al., "Evaluating the validity of animal models for research into therapies for immune-based disorders," DDT, 2004, vol. 9(12), pp. 517-524.
Abraha et al., "C-terminal inhibition of tau assembly in vitro and in Alzheimer's disease," Journal of Cell Science, 2000, vol. 113, pp. 3737-3745.
Acharya et al., "Solid-phase synthesis of substituted imidazoline-tethered 2,3-diketopiperazines, cyclic ureas, and cyclic thioureas," J Comb Chem, Nov.-Dec. 2001, vol. 3(6), pp. 612-623.
Adorini, L., "Selective immunointervention in autoimmune diseases: lessons from multiple sclerosis," J Chemother, Jun. 2001, vol. 13(3), pp. 219-234 (Abstract Only Provided).
Akiyama et al., "Inflammation and Alzheimer's disease," Neurobiol Aging, 2000, vol. 21, pp. 383-421.
Albert et al., "ABT-491, a highly potent and selective PAF antagonist, inhibits nasal vascular permeability associated with experimental allergic rhinitis in Brown Norway rats," Inflamm. Res., 1997, Supplement 2, pp. S133-S134.
Alvarez et al., "Isolation and Structure Elucidation of Two New Calpain Inhibitors from Streptomyces Griseus," J. Antibiotics, Nov. 1994, vol. 47(11), pp. 1195-1201.
Andreasen et al., "Cerebrospinal fluid beta-amyloid (1-42) in Alzheimer disease: differences between early- and late-onset Alzheimer disease and stability during the course of disease," Arch. Neurol., Jun. 1999, vol. 56(6), pp. 673-680.
Arbabi et al., "Priming Interleukin 8 Production: Role of Platelet-Activating Factor and p38," Arch Surg., Dec. 1999, vol. 134(12), pp. 1348-1353.
Ashwood et al. "Is autism an autoimmune disease?" Autoimmunity Reviews, Nov. 2004, vol. 3, No. 7-8, pp. 557-562.
Au et al., "Effect of PDE4 Inhibitors on Zymosan-Induced IL-8 Release From Human Neutrophils: Synergism with Prostanoids and Salbutamol," Br. J. Pharmacol, 1998, vol. 123, pp. 1260-1266.
Auci et al. "Methylphenidate and the immune system," J Am Acad Child Adolcesc Psychiatry 1997, 36(8): 1015-1016.
Auerbach et al., "Angiogenesis Assays: A Critical Overview," Clinical Chemistry, 2003, vol. 49, No. 1, pp. 32-40.
Bagaria et al., "Cyclo(L-leucyl-alpha,beta-dehydrophenylalanine): the first diketopiperazine containing an alpha,beta-dehydrophenylalanine residue," Acta Crystallogr C., Mar. 2005, vol. 61(Pt 3), pp. 174-176, Epub Feb. 28, 2005.
Baig et al., "High Performance Liquid Chromatography as a Tool in the Definition of Abnormalities in Monamine and Tryptophan Metabolites in Cerebrospinal Fluid from Patients with Neurological Disorders," Biomed Chromatogr 1991, 5(3):108-112 (Abstract Only Provided).
Balk, "Lesson 24, vol. 12—ARDS: Pathophysiology of SIRS and MODS" www.chestnet.org/education/pccu/vol12/ lesson24.html, pp. 1-19, printed Jul. 20, 2000.
Banks et al., "Radioactively Iodinated Cyclo(His-Pro) Crosses the Blood-Brain Barrier and Reverses Ethanol-Induced Narcosis," Am J Physiol, May 1993, vol. 264(5 Pt. 1), pp. E723-E729 (Abstract Only Provided).
Bar-Or et al. "Commercial human albumin preparations for clinical use are immunosuppressive in vitro," Critical Care Medicine, Jun. 2006, vol. 34, No. 6, pp. 1707-1712 (Abstract Only) (downloaded from : journals.lww.com).
Bar-Or et al., "An Analog of the Human Albumin N-Terminus (Asp-Ala-His-Lys) Prevents Formation of Copper-Induced Reactive Oxygen Species," Biochemical and Biophysical Research Communications, 2001, vol. 284(3), pp. 856-862.
Bar-Or et al., "Potential Plasma Surrogate Biomakers for CNS Demyelinating Processes," 19th Congress of the European Committee for Treatment and Research in Multiple Sclerosis Meeting; Sep. 17-20, 2003; 2 pp.
Barrow et al., WIN 64821, a New Competitive Antagonist to Substance P, Isolated from an *Aspergillus* Species: Structure Determination and Solution Conformation, J. Org. Chem., 1993, vol. 58, pp. 6016-6021.
Battersby et al., "Diketopiperazine Formation and N-Terminal Degradation in Recombinant Human Growth Hormone," Int. J. Pept. Protein Res, Sep. 1994, vol. 44(3), pp. 215-222 (Abstract Only Provided).
Beger et al, "Treatment of Pancreatic Cancer: Challenge of the Facts," World Journal of Surgery, 2003, vol. 27, No. 10, pp. 1075-1084.
Berman et al., "Psoriasis," PubMed Health, reviewed Nov. 22, 2011, available at www.ncbi.nlm.nih.gov/pubmedhealth/PMH0001470/?report=printable.
Berry et al., "Inhibition of Tau Polymerization by its Carboxy-Terminal Caspase Cleavage Fragment," Biochemistry, 2003, vol. 42, pp. 8325-8331.
Bhargava et al., "Inhibition of Neuroleptic-Induced Dopamine Receptor Supersensitivity by Cyclo (Leu-Gly)," Pharmacol Biochem Behav, Nov. 1980, vol. 13(5), pp. 633-636 (Abstract Only Provided).
Bhargava, "Antagonism of ketamine-induced anesthesia and hypothermia by thyrotropin releasing hormone and cyclo (His-Pro)," Neuropharmacology, 1981, vol. 20(7), pp. 699-702.
Bhargava, "Inhibition of abstinence syndrome in opiate dependent mice by cyclo (His-Pro)," Life Sci, 1981, vol. 28(11), pp. 1261-1267.
Bhargava, "The effect of melanotrophin release inhibiting factor (MIF) and cyclo (Leu-Gly) on the tolerance to morphine-induced antinociception in the rat: a dose-response study," Br J Pharmacol, Apr. 1981, vol. 72(4) (Abstract Only Provided).
Bhargava, "The effects of thyrotropin releasing hormone and histidyl-proline diketopiperazine on delta-9-tetrahydrocannabinol-induced hypothermia," Life Sci, 1980, vol. 26(11), pp. 845-850.
Bielekova et al., "Development of biomarkers in multiple sclerosis," Brain, Jul. 2004, vol. 127(Pt 7), pp. 1463-1478, Epub Jun. 4, 2004.
Binisti et al., "Structure-Activity Relationships in Platelet Activating Factor," J. Lipid Mediat. Cell Signal, Jan. 1997, vol. 15(2), pp. 125-144 (Abstract Only Provided).
Blazickova et al., "Immunomodulatory Characteristics of Synthetic Cyclic Dipeptides," Int. J. Immunotherapy, 1994, vol. 10(3), pp. 89-93.
Borthwick, "2,5-Diketopiperazines: Synthesis, Reactions, Medicinal Chemistry, and Bioactive Natural Products," Chemical Reviews, 2012, vol. 112, Iss. 7, pp. 3641-3716.

(56) References Cited

OTHER PUBLICATIONS

Bowden et al., "Re-evaluation of histidyl-proline diketopiperazine [cyclo (His-Pro)] effects on food intake in the rate," Pharmacol. Biochem. Behav., Feb. 1988, vol. 29(2), pp. 357-363 (Abstract Only Provided).
Braun-Moscovici et al., "Stem cell therapy in scleroderma," Current Opinion in Rheumatology, 2002, vol. 14, Iss.6, pp. 711-716.
Brauns et al., "Selected cyclic dipeptides inhibit cancer cell growth and induce apoptosis in HT-29 colon cancer cells," Anticancer Research, 2004, vol. 24, pp. 1713-1720.
Breitbart et al., "A randomized, double-blind, placebo-controlled trial of psychostimulants for the treatment of fatigue in ambulatory patients with human immunodeficiency virus disease", Arch Inern Med 2001, 161(3): 411-20, Abstract only, PubMed ID: 11176767.
Bressan et al., "Coordination chemistry of peptides. Part II. Crystal structure of cyclo-L-methionylglycine and studies of metal complexation," Int J Pept Protein Res, Apr. 1982, vol. 19(4) (Abstract Only Provided).
Bresser et al., "T-Cell Activation in the Lungs of Patients With Systemic Sclerosis and Its Relation With Pulmonary Fibrosis," Chest, Jul. 2001, 6 pages.
Bruera et al., Patient-Controlled Methylphenidate for the Management of Fatigue in Patients With Advanced Cancer: A Preliminary Report, Journal of Oncology, vol. 21, No. 23, Dec. 2003, pp. 4439-4443.
Bunn, "Early detection of lung cancer using serum RNA or DNA markers: ready for "prime time" or for validation?," J Clin Oncol., Nov. 1, 2003, vol. 21(21), pp. 3891-3893.
Caballero et al., "Brief synthesis of the cell cycle inhibitor tryprostatin B and its alanine analogue," Fourth International Electronic conference of Synthetic Organic Chemistry (ECXOC-4), Sep. 1-13, 2000, 4 pages, available at pages.unibas.ch/mdpi/eecxoc-4/c0023/c0023.htm.
Caballero et al., "Brief total synthesis of the cell cycle inhibitor tryprostatin B and related preparation of its alanine analogue," J Org Chem, Sep. 5, 2003, vol. 68(18) (Abstract Only Provided).
Carlton et al., "Attenuation of alcohol-induced hypothermia by cycle (His-Pro) and its analogs," Neuropeptides, Jun. 1995, vol. 28(6), pp. 351-355 (Abstract Only Provided).
Chabner et al., "Chemotherapy and the war on cancer," Nature Reviews Cancer, 2005, vol. 5, Iss. 1, pp. 65-72.
Challman et al., "Methylphenidate: its pharmacology and uses", Mayo Clin Proc 2000, 75: 711-721.
Chan, "Chapter 9: Transplant Rejection and Its Treatment," Atlas of Diseases of the Kidney, vol. 5, (Ed.Henrich et al.), Wiley-Blackwell, 1999, pp. 9.1-9.13.
Chan et al., "Site-Specific N-Terminal Auto-Degradation of Human Serum Albumin," Eur. J. Biochem., 1995, vol. 227, pp. 524-528.
Chen et al., "Up-regulation of Platelet-activating Factor Receptors in Lung and Alveolar Macrophages in the Bleomycin-Hamster Model of Pulmonary Fibrosis," J. Pharmacol. Exp. Ther., 1997, vol. 280(3), pp. 1219-1227.
Cho et al., "Contribution of Natural Inhibitors to the Understanding of the PI3K/PDK1/PKB Pathway in the Insulin-mediated Intracellular Signaling Cascade," Int. J. Mol. Sci., 2008, vol. 9, pp. 2217-2230.
Chou et al., "Structure-Activity Relationships of Substituted Benzothiophene-anthranilamide Factor Xa Inhibitors," Bioorganic & Medicinal Chemistry Letters, 2003, vol. 13. Iss. 3, pp. 507-511.
Ciarkowski et al., "Conformation of cyclo-(D-phenylalanyl-trans-4-fluoro-D-prolyl)," Int. J. Pept. Protein Res., vol. 36, Sep. 1990, pp. 285-291.
Clark et al., "Roquefortine E, a Diketopiperazine from an Australian Isolate of Gymnoascus reessii," J. Nat. Prod., 2005, vol. 68(11), p. 1661-1664 (Abstract Only Provided).
Cody et al., "The design of potent and selective inhibitors of thrombin utilizing a piperazinedione template: part 2," Bioorg Med Chem Lett, Sep. 6, 1999, vol. 9(17), pp. 2503-2508.
Coggins et al., "High Affinity Specific Binding of the Thyrotrophin Releasing Hormone Metabolite Histidylproline to Rat Brain Membranes," Neuropeptides, Jan. 1987, vol. 9(1), pp. 83-91 (Abstract Only Provided).
Cole et al., "Potential Tumor-Selective Nitroimidazolylmethyluracil Prodrug Derivatives: Inhibitors of the Angiogenic Enzyme Thymidine Phosphorylase," Journal of Medicinal Chemistry, 2003, vol. 46, Iss. 2, pp. 207-209.
Costa et al., "Aggregation of features of the metabolic syndrome is associated with increased prevalence of chronic complications in Type 2 diabetes," Diabetic Medicine, 2004, vol. 21, Iss. 3, 252-255.
Couladouros et al., "Solid-phase total synthesis of (-)-Phenylhistine and (-)-Aurantiamine. Synthesis of a diverse dehydro-2,5-diketopiperazine library. Part II," Mol Divers., 2005, vol. 9(1-3), pp. 111-121.
Crowe et al., "The N Terminal Region of Human Tau is Present in Alzheimer's Disease Protein A68 and is Incorporated into Paired Helical Filaments," American Journal of Pathology, 1991, vol. 139(6), pp. 1463-1470.
Cruse et al., "Illustrated Dictionary of Immunology" Second Edition, 2003, pp. 192, 260, 530-531.
Cruse et al., Illustrated Dictionary of Immunology (2nd edition, Taylor & Francis Group, CRC Press LLC, 2003), p. 475.
Cui et al., "Novel Mammalian Cell Cycle Inhibitors, Tryprostatins A, B and Other Diketopiperazines Produced by Aspergillus fumigatus II. Physico-chemical properties and Structures," The Journal of Antibiotics, Jun. 1996, pp. 534-540.
D'Alagni et al. "Effect of Urea on the Optical Rotatory Dispersion of Diketopiperazines of ISerine, I-Alanine, I-Lysine, I-Valine, and I-Valylglycine." The Journal of Biological Chemistry, Nov. 10, 1969, vol. 244, No. 21, pp. 5843-5848.
Davidson et al., "Autoimmune Diseases," N. Engl. J. Med, 2001, vol. 345(5), pp. 340-350.
Davies et al., "Synthesis of Methylphenidate Analogues and their Binding Affinities at Dopamine and Serotonin Transport Sites", Bioorganic & Medicinal Chemistry Letters, 2004, vol. 14, pp. 1799-1802.
De La Cruz et al, "Effect of WEB 2086-BS, an antagonist of platelet-activating factor receptors, on retinal vascularity in diabetic rats," European Journal of Pharmacology, 1998, vol. 360, Iss. 1, pp. 37-42.
Degrassi et al., "Plant Growth-Promoting Pseudomonas putida WCS358 Produces and Secretes Four Cyclic Dipeptides: Cross-Talk with Quorum Sensing Bacterial Sensors," Current Microbiology, 2002, vol. 45, pp. 250-254.
Denault et al., "Transcriptional activation of the interleukin-8 gene by platelet-activating factor in human peripheral blood monocytes," Immunology, 1997, vol. 91, pp. 297-302.
Deutsch et al., "Synthesis and pharmacology of potential cocaine antagonists. 2. Structure-activity relationship studies of aromatic ring-substituted methylphenidate analogs," J Med Chem 1996, vol. 39, pp. 1201-1209.
Diamanti et al., "Distribution and Characterization of Cyclo (His-Pro)-like Immunoreactivity in the Human Gastrointestinal Tract," Neuropeptides, Mar. 1985, vol. 6(1):21-5 (Abstract Only Provided).
Dirr, K. et al., "The transformation of arginine into citrulline," Z. Physiol. Chem., 1935, vol. 237, pp. 121-130.
Dorwald, "Side Reactions in Organic Synthesis." Wiley-VCH, Copyrighted May 5, 2005, p. IX of Preface, pp. 1-15.
Dunnick et al., "Decreased incidence of spontaneous mammary gland neoplasms in female F344 rats treated with amphetamine, methylphenidate, or codence," Cancer Letters, 1996, vol. 102(1-2), pp. 77-83.
Dunnick et al., "Experimental studies on long-term effects of methylphenidate hydrochloride," Toxicology 1995, 103(2): 77-84 Abstract only, PubMed ID: 8545847.
Duntas et al., "A Fast Protein Liquid Chromatography (FPLC) Method for Study of Thyrotropin-releasing Hormone (TRH) and its metabolite Histidyl-Proline Diketopiperazine (CHP) in Human Blood: Degradation in Liver and Pancreatic Diseases," Neuropeptides, 1993, vol. 25(6), pp. 357-361 (Abstract Only Provided).

(56) References Cited

OTHER PUBLICATIONS

Esposito et al., "The Solution Structure of the C-Terminal Segment of Tau Protein," Journal of Peptide Science, 2000, vol. 6, pp. 550-559.
Evans et al. "Metabolic effects of platelet-activating factor in rats in vivo: Stimulation of hepatic glycogenolysis and lipogenesis." Biochemical Journal, Jul. 1990, vol. 269, No. 1, pp. 269-272.
Faden et al., "Neuroprotective and nootropic actions of a novel cyclized dipeptide after controlled cortical impact injury in mice." J. Cerebral Blood Flow & Metabolism, 2003, vol. 23, pp. 355-363.
Faden et al., "Novel diketopiperazine enhances motor and cognitive recovery after traumatic brain injury in rats and shows neuroprotection in vitro and in vivo," J. Cerebral Blood Flow & Metabolism, 2003, vol. 23, pp. 342-354.
Faden et al., "Novel neuroprotective Tripeptides and Dipeptides," Ann. N.Y. Acad. Sci, 2005, vol. 1053, pp. 472-481.
Faden et al., "Novel small peptides with neuroprotective and nootropic properties," J. Alzheimer's Dis, 2004, vol. 6, pp. S93-S97.
Faden et al., "Novel TRH analog improves motor and cognitive recovery after traumatic brain injury in rodents," Am J Physiol, Oct. 1999, vol. 277(4 Pt 2), pp. R1196-R1204.
Fdhila et al., "dd-diketopiperazines: antibiotics active against Vibrio anguillarum isolated form marine bacteria associated with cultures of Pecten maximus" J Nat Prod, Oct. 2003, vol. 66(10) (Abstract Only Provided).
Fischer, "Diketopiperazines in Peptide and Combinatorial Chemistry," Journal of Peptide Science, 2003, vol. 9, pp. 9-35.
Fisher et al., "The epidemiology of non-Hodgkin's lymphoma," Oncogene, 2004, vol. 23, Iss. 38, pp. 6524-6534.
Folkes et al., "Synthesis and in vitro evaluation of a series of diketopiperazine inhibitors of plasminogen activator inhibitor-1," Bioorg Med Chem Lett, Oct. 2001, vol. 11(19), pp. 2589-2592 (Abstract Only Provided).
Fragner et al., "A New Biological Contribution of Cyclo(His-Pro) to the Peripheral Inhibition of Pancreatic Secretion," Am J Physiol, Dec. 1997, vol. 273(6 Pt. 1), pp. E1127-E1132 (Abstract Only Provided).
Gamblin et al., "Tau Polymerization: Role of the Amino Terminus," Biochemistry, 2003, vol. 42(7), pp. 2252-2257.
Garcia-Sierra et al., "Conformational Changes and Truncation of Tau Protein during Tangle Evolution in Alzheimer's Disease," Journal of Alzheimer's Disease, 2003, vol. 5, pp. 65-77.
Gatley et al., "Affinities of Methylphenidate derivative for dopamine, norepinephrine and seotonin transporters," Life Sciences 1996, 58(12): 231-239.
Glavin et al. "Effects of Dopamine Agonists and Antagonists on Gastric Acid Secretion and Stress Responses in Rats." Life Sciences, 1987, vol. 41 No. 11, p. 1397-1408.
Gomez et al., "Low-Dose Dopamine Agonist Administration Blocks Vascular Endothelial Growth Factor (VEGF)-Mediated Vascular Hyperpermeability without Altering VEGF Receptor 2-Dependent Luteal Angiogenesis in a Rat Ovarian Hyperstimulation Model," Endocrinology, 2006, vol. 147, No. 11, pp. 5400-5411.
Goolcharran et al., "Comparison of the Rates of Deamidation, Diketopiperazine Formation and Oxidation in Recombinant Human Vascular Endothelial Growth Factor and Model Peptides," AAPS PharmSci, 2000 vol. 2(1), p. E5 (Abstract Only Provided).
Gorbitz "Crystal and Molecular Structure of cyclo-L-Aspartyl-L-alanyl (3,6-Dioxo-5-methyl-2-piperazineacetic acid)" Acta Chemica Scandinavica B, 1987, vol. 41, pp. 83-86.
Gorbitz, "Crystal and molecular structures of the isomeric dipeptides alpha-L-aspartyl-L-alanine and beta-L-aspartyl-L-alanine," Acta Chem Scand B., vol. 41(9), Oct. 1987, pp. 679-685.
Gordon et al, "Reductive Alkylation on a Solid Phase: Synthesis of a Piperazinedione Combinatorial Library," Bioorganic & Medicinal Chemistry Letters, 1995, vol. 5, No. 1, p. 47-50.
Gountopoulou et al. "TNFα is a potent inducer of platelet-activating factor synthesis in adipocytes but not in preadipocytes. Differential regulation by PI3K," Cytokine, Jan. 2008, vol. 41, No. 2 p. 174-181, (Abstract Only).
Graz et al "Cyclic Dipeptides in the Induction of Maturation for Cancer Therapy," J. Pharm. Pharmacol., 2000, vol. 52, pp. 75-82.
Graz et al., "Mechanism of a anti-fungal action of selected cyclic dipeptides," Pharmazie, Nov. 2001, vol. 56(11), pp. 900-901.
Gross et al., "Regulation of Interleukin-8 Production in a Human Colon Epithelial Cell Line (HT-29)," Gastroenterology, 1995, vol. 108, pp. 653-661.
Grubek-Jaworska et al., "CD4/CD8 lymphocytes in BALF during the efferent phase of lung delayed-type hypersensitivity reaction induced by single antigen inhalation," Med Sci Monit, Sep.-Oct. 2001, vol. 7(5), pp. 878-883 (Abstract Only Provided).
Gu et al., "Diketopiperazine Formation, Hydrolysis, and Epimerization of the New Dipeptide Angiotensin-Converting Enzyme Inhibitor RS-10085," Pharm Res, 1987, vol. 4(5), pp. 392-397 (Abstract Only Provided).
Gudasheva et al., "Anxiolytic activity of endogenous nootropic dipeptide cycloprolylglycine in elevated plus-maze test," Bull Exp Biol Med, May 2001, vol. 131(5) (Abstract Only Provided).
Gudasheva et al., "Identification of a novel endogenous memory facilitating cyclic dipeptide cyclo-prolylglycine in rat brain," FEBS Lett, Aug. 5, 1996, vol. 391(1-2) (Abstract Only Provided).
Guerra et al., "PEGylation Prevents the N-Terminal Degradation of Megakaryocyte Growth and Development Factor," Pharm Res, 1998, vol. 15(12), pp. 1822-1827 (Abstract Only Provided).
Gura, "Systems for Identifying New Drugs are Often Faulty," Science, 1997, vol. 278, No. 5340, pp. 1041-1042.
Gustafson, "Adipose Tissue, Inflammation and Atherosclerosis," J. Atheroscler. Thromb., Apr. 30, 2010, vol. 17(4), pp. 332-341.
Hansel et al. "Metabolic Syndrome is Associated with Elevated Oxidative Stress and Dysfunctional Dense High-Density Lipoprotein Particles Displaying Impaired Antioxidative Activity." The Journal of Clinical Endocrinology & Metabolism, Oct. 2004, vol. 89, No. 10, pp. 4963-4971.
Happe, "Excessive daytime sleepiness and sleep disturbances in patients with neurological diseases: epidemiology and management", Drugs 2003, 63(24): 2725-2737 Abstract only, PubMed ID 14664652.
Haran "Beyond just tired: figuring out MS-related fatigue", available on the Worldwide Web at www.understandingsms.com/ms/articles/ms_beyondtired.asp, downloaded on May 7, 2006.
Hasegawa et al., "Protein Sequence and Mass Spectrometric Analysis of Tau in the Alzheimer's Disease Brain," Journal of Biological Chemistry, 1992, vol. 267(24), pp. 17047-17054.
Hayashi et al., "Synthetic Hexa- and Heptapeptides That Inhibit IL-8 from Binding to and Activating Human Blood Neutrophils1," J. Immunol., 1995, vol. 154, pp. 814-824.
Hilton et al., "Food Contains the Bioactive Peptide, Cyclo(His-Pro)," J. Clin Endocrinol Metab, Aug. 1992, vol. 75(2), pp. 375-378 (Abstract Only Provided).
Hilton et al., "Identification and Characterization of Cyclo (His-Pro)-Like Immunoreactivity in Amniotic Fluid," Peptides, Mar.-Apr. 1989, vol. 10(2), pp. 299-301 (Abstract Only Provided).
Hilton et al., "Radioimmunoassay of Cyclo(His-Pro) in Unextracted Human Plasma: Report of a Normal Range and Definition of Factors Critical for Successful Assay," Neuropeptides, 1989, vol. 13(1), pp. 65-70 (Abstract Only Provided).
Hilton et al., "Relationship between Plasma Cyclo (His-Pro), a Neuropeptide Common to Processed Protein-Rich Food, C-Peptide/Insulin Molar Ratio in Obese Women," Nutr Neurosci, 2001, vol. 4(6), pp. 469-474 (Abstract Only Provided).
Hlinak et al., "Effect of alaptide, its analogues and oxiracetam on memory for an elevated plus-maze in mice," European Journal of Pharmacology, 1996, vol. 314, pp. 1-7.
Hoffman et al., "An Enzymatically Stable Peptide with activity in the Central Nervous System: Its Penetration through the Blood-CSF Barrier," Brain Res, Feb. 11, 1977, vol. 122(1), pp. 87-94 (Abstract Only Provided).
Holden et al., "Quorum-sensing cross talk: isolation and chemical characterization of cyclic dipeptides from Pseudomonas aeruginosa and other Gram-negative bacteria," Moleclur Microbiology, 1999, vol. 33(6), pp. 1254-1266.

(56) References Cited

OTHER PUBLICATIONS

Hong et al., "Inhibitory effect against Akt of cyclic dipeptides isolated from *Bacillus* sp" J. Microbiol. Biotechnol., 18, 682-685 (2008).
Houston et al., "The cyclic dipeptide CI-4 [cyclo-(I-Arg-d-Pro)] inhibits family 18 chitinases by structural mimicry of a reaction intermediate," Biochem J., Nov. 15, 2002, vol. 368(Pt 1) (Abstract Only Provided).
Horwitz et al., "Piperazinedione plus total body irradiation: an alternative preparative regimen for allogeneic bone marrow transplantation in advanced phases of chronic myelogenous leukemia," Bone Marrow Transplantation, 1989, vol. 4, Iss. 1, pp. 101-105.
Hwang et al., "Effects of cyclo (his-pro) plus zinc on glucose metabolism in genetically diabetic obse mice," Diabetes Obes. Metab., Sep. 2003, vol. 5(5), pp. 317-324 (Abstract Only Provided).
Iriuchijima et al., "Thyrotripin-Releasing Hormone and Cyclo (His-Pro)-Like Immunoreactivities in the Cerebrospinal Fluids of 'Normal' Infants and Adults, and Patients with Various Neuropsychiatric and Neurologic Disorders," Life Sci. 1987, 41(22):2419-2428, Abstract only, from PubMed—PMID:2891013.
Ishibashi et al., "A Mechanism for Bitter Taste Sensibility in Peptides," Agric. Biol. Chem., 1988, vol. 52(3), pp. 819-827.
Ishibashi et al., "Bitterness of Leucine-Containing Peptides," Agric. Biol. Chem., 1987, vol. 51 (9), pp. 2389-2394.
Ishii, et al. "Incidence of brain tumors in rats fed aspartame," Toxicology Letters, 1981, vol. 7, pp. 433-437.
Iyer et al. "Inflammatory lipid mediators in adipocyte function and obesity." Nature Reviews Endocrinology, Feb. 2010, vol. 6, pp. 71-82.
Jackson et al., "Amyotrophic Lateral Sclerosis: Thryrotropin-releasing hormone and histidyl proline diketopiperazine in the spinal cord and cerebrospinal fluid," Neurology, 1986, vol. 36(9), pp. 1218-1223.
Jamie et al., "The effect of the isomers of cyclo(Trp-Pro) on heart and ion-channel activity," J Pharm Pharmacol, Dec. 2002, vol. 54(12) (Abstract Only Provided).
Jara et al., "Elevated serum levels of cyclo (His-Pro), and endogenous inhibitor ofpituitary prolactin secretion, in systemic lupus erythematosus patients," Lupus, 1997, vol. 6(3) (Abstract Only Provided).
Jaspan et al., "Study of Passage of Peptides Across the Blood-Brain Barrier: Biological Effects of Cyclo(His-Pro) After Intravenous and Oral Administration," Annals of the New York Academy of Science, 1994, vol. 739, pp. 101-107 (Abstract Only Provided).
Jiang et al. "Asymmetric Reformastky reaction catalyzed by amino acid derivatives," Huaxue Tongbao CKNI, 2001, vol. 10, pp. 637-640 (English Abstract).
Jiang et al., "AKT signaling in regulating angiogenesis," Current Cancer Drug Targets, 2008, vol. 8, pp. 19-26.
Jicha et al., "Sequence Requirements for Formation of Conformational Variants of Tau Similar to Those Found in Alzheimer's Disease," Journal of Neuroscience Research, 1999, vol. 55, pp. 713-723.
Johnson et al., "Relationships between drug activity in NCI preclinical in vitro and in vivo models and early clinical trials," British Journal of Cancer, 2001, vol. 84, Iss. 10, pp. 1424-1431.
Kaakkola et al., "Effects of two diketopiperazines, cyclo (His-Pro) and cyclo (Asp-Phe), on striatal dopamine: A microdialysis study," Brain Research Bulletin, 1993, vol. 32(6), pp. 667-672.
Kanzaki et al., "Enzymatic synthesis of dehydro cyclo(His-Phe)s, analogs of the potent cell cycle inhibitor, dehydrophenylahistin, and their inhibitory activities toward cell division," Biosci Biotechnol Biochem, Nov. 2004, vol. 68(11), pp. 2341-2345 (Abstract Only Provided).
Kasperska-Zajac et al. "Platelet Activating Factor as a Mediator and Therapeutic Approach in Bronchial Asthma." Inflammation, Apr. 2008, vol. 31, No. 2, pp. 112-120.
Kikwai et al, "Stability and degradation profiles of Spantide II in aqueous solutions," Eur J Pharm Sci, Feb. 2006, vol. 27(2-3), pp. 158-166, Epub Nov. 2, 2005. (Abstract Only Provided).

Kilian et al., "Biological activity of selected tyrosine-containing 2,5-diketopiperazines," Pharmazie, Apr. 2005, vol. 60(4), pp. 305-309 (Abstract Only Provided).
Kilian et al., "The effect of the isomer of cyclo(Trp-Pro) on heart and ion-channel activity," J. Pharm. Pharmacol., Dec. 2002, vol. 54(12), pp. 1659-1665 (Abstract Only Provided).
Kobayashi et al., "Neuropeptide Y and histidyl-proline diketopiperazine," Rinsho-Kensa, Japan, Sep. 1987, vol. 21, No. 9, pp. 984-991.
Kopple et al. "Conformation of Cyclo-(I-Threonine)2 and Cyclo-(I-Allo Threonine)2 : A Proton and Carbon N.m.r. Study." International Journal of Peptide Protein Research, Jul. 1981, vol. 18, No. 1, pp. 33-40.
Koskinen, "Effect of Low Intravenous Doses of TRH, Acid-TRH and Cyclo (His-Pro) on Cerebral and Peripheral Blood Flows," British Journal of Pharmacology, 1986, vol. 87(3), pp. 509-519 (Abstract Only Provided).
Kow et al., "The Effects of the TRH Metabolite Cyclo(His-Pro) and Its Analogs on Feeding," Pharmacology, Biochemistry & Behavior, 1991, vol. 38, pp. 359-364.
Krim, Lori, Thesis (Ph.D. In Chemistry) (2001), University of Pennsylvania, Chemistry Library Reading Room (Call No. QD001 2001.K92), University Microfilms Order No. 3031684, ISBN 0-493-44179-4, 762 pages.
Krupp et al., "Fatigue in multiple sclerosis," Curr Neurol Neurosci Rep 2001, 1(3): 294-298.
Kuenz et al., "Plasma levels of soluble adhesion molecules sPECAM-1, sP-selectin and sE-selectin are associated with relapsing-remitting disease course of multiple sclerosis," J. Neuroimmunol, Oct. 2005, vol. 167(1-2), pp. 143-149.
Kulikov et al., "Review: The Bioregulatory Role of Platelet-Activating Factor in Intracellular Processes and Cell-Cell Interactions," 1997, www.protein.bio.msu.su/biokhimiya/contents/v63/full/63010057.html, pp. 1-13.
Kurahashi et al., "Histydyl-Proline Diketopiperazine (HPD), A Metabolite of Thyrotropin-Releasing Hormone (TRH), Improves the Ataxic Gait in 3-Acetylpyridine (3-AP) Treated Rats," No To Shinkei, Sep. 1986, vol. 38(9), pp. 893-898 (Abstract Only Provided).
Leaf, "The War on Cancer," Fortune, Mar. 9, 2004, 13 pages.
Leonard et al., "Methylphenidate: a review of its neuropharmacological, neuropsycological and adverse clinical effects," Human Psychopharmacol Clin Exp 2004, 19:151-180.
Larsen et al. "Kinetics of degradation and oil solubility of ester prodrugs of a model dipeptide (Gly-Phe)," Eur J Pharm Sci, Aug. 2004, vol. 22(5), pp. 399-408 (Abstract Only Provided).
Lechan et al., "Thyrotropin Releasing Hormone but not Histidyl-Proline Diketopiperazine is Depleted from Rat Spinal Cord Following 5,7-Dihydroxytryptamine Treatment," Brain Research, 1985, vol. 326(1), pp. 152-155 (Abstract Only Provided).
Lechin et al., "Plasma Neurotransmitters and Cortisol in Chronic Illness: Role of Stress," J Medicine, 1994, vol. 25(3-4), pp. 181-192 (Abstract Only Provided).
Leduque et al., "Histidyl-Proline Diketopiperazine (His-Pro DKP) Immunoreactivity is Present in the Glucagon-Containing Cells of the Human Fetal Pancreas," J Clin Invest, 1987, 79(3):875-880 (Abstract Only Provided).
Lee et al., "Characterization of an Elastase Inhibitor Produced by Streptomyces lavendulae SMF11," Journal of Microbiology and Biotechnology, 2000, vol. 10, No. 1, pp. 81-85.
Lee et al., "Cyclo (Leu-Gly attenuates the striatal dopaminergic supersensitivity induced by chronic morphine," Alcohol Drugs Res, 1987, vol. 7(1) (Abstract Only Provided).
Lehninger et al., "Amino Acids and Peptides," Chapter 5 of Principles of Biochemistry, 1993, 2nd edition, pp. 111-133.
Lindner et al., "[Effects of cyclic adenosine-3',5'-monophosphate and cyclo{Lys-Pro}.HCl neuronotrophic factors in tissue culture]," J Hirnforsch, 1987, vol. 28(3) (Abstract Only Provided).
Liu et al., "Hydroxyprolylserine derivatives JBP923 and JBP485 exhibit the antihepatitis activities after gastrointestinal absorption in rats," J Pharmacol Exp Ther, Aug. 2000, vol. 294(2) (Abstract Only Provided).

(56) References Cited

OTHER PUBLICATIONS

Luca et al., "Determination of serotonin content and ceruloplasmin activity, of blood and CSF amino acid level in multiple sclerosis," Neurol Psychiatr (Bucur), 1986, vol. 24(3), pp. 153-159.

Lucietto et al., "The biological activity of the histidine-containing diketopiperazines cyclo (His-Ala) and cyclo (His-Gly)," Peptides, Nov. 2006, vol. 27(11), pp. 2706-2714, Epub Jun. 21, 2006 (Abstract Only Provided).

Martin et. al. "Do Structurally Similar Molecules Have Similar Biological Activity?" Journal of Medicinal Chemistry, 2002, vol. 45, pp. 4350-4358.

Mayer, "Immunology—Chapter Four," Immunoglobulins—Structure and Function, online at pathmicro.med.sc.edu/mayer/IgStruct2000.htm, University of South Carolina School of Medicine, Nov. 6, 2009, 8 pages.

Marek "Psychotropic drugs and inflammatory reaction (III): Effects of single and repeated administration of psychotropic drugs on the bentonite oedema of the rat paw." Activas Nervosa Superior, 1985, vol. 27, No. 1, p. 21-22.

Mazza et al., "Potential energy calculations on phenylalanine rotamers in different boat forms of proline-containing cyclic dipeptides," Int. J. Pept. Protein Res., vol. 31, Feb. 1988, pp. 157-163.

McCain et al., "Endorphinergic modulation of immune function: potent action of the dipeptide glycyl-L-glutamine," Life Science, 1987, vol. 41, pp. 169-176.

McCain et al., "Modulation of Human T-Cell Suppressor Activity by Beta Endorphin and Glycyl-L-Glutamine," Int. J. Immunopharmoc, 1986, vol. 8(4), pp. 443-446.

McCleland et al., "An investigation into the biological activity of the selected histidine-containing diketopieperazines cyclo(His-Phe) and cyclo(His-Tyr)," Journal of Pharmacy and Pharmacology, Sep. 2004, vol. 56(9), pp. 1143-1153.

Meester et al., "In Vivo Inhibition of Dipeptidyl Peptidase IV Activity by Pro-Pro-diphenyl-phosphonate (Prodipine)," Biochemical Pharmacology, 1997, vol. 54, pp. 173-179.

Meltzer et al. "The synthesis of bivalent 2β-carbomethoxy-3β-(3,4-dichlorophenyl)-8-heterobicyclo[3.2.1]octanes as probes for proximal binding sites on the dopamine and serotonin transporters" Bioorganic and Medicinal Chemistry, Feb. 15, 2008, 16, 1832-1841.

Mentlein et al., "Dipeptidyl-Peptidase IV Hydrolyses Gastric Inhibitory Polypeptide, Glucagon-Like Peptide-1(7-36)amide, Peptide Histidine Methionine and is Responsible for their Degradation in Human Serum," European Journal of Biochemistry, 1993, vol. 214(3), pp. 829-835 (Abstract Only Provided).

Mesh, "Autoimmune Diseases," internet document www.ncbi.nlm.nih.gov/sites/entrez, accessed Oct. 31, 2007, 2 pages.

Michell et al., "Biomarkers and Parkinson's Disease," Brain, Aug. 2004, vol. 127, pp. 1693-1705.

Miller et al., "Peptide Inhibitor of Interleukin-8 (IL-8) Reduces Staphylococcal Enterotoxin-A (SEA) Induced Neutrophil Trafficking to the Lung," Inflamm. Res., 1996, vol. 45, pp. 393-397.

Milne, et al. "The biological activity of selected cyclic dipeptides," J. Pharm. Pharmacol., 1998, vol. 50, pp. 1331-1337.

Minelli et al., "Phosphoproteomic analysis of the effect of cyclo-[His-Pro] dipeptide on PC12 cells." Peptides, Jan. 2006;27(1):105-13. Epub Aug. 30, 2005., Abstract only PMID: 16137790.

Mitsuma et al., "Radioimmunoassay for Thyrotropin-Releasing Hormone Precursor Peptide, Lys-Arg-Gln-His-Pro-Gly-Arg-Arg," Exp Clin Endocrinology, 1989, vol. 93(1), pp. 53-60 (Abstract Only Provided).

Mizuma et al., "Concentration-Dependent Preferences of Absorptive and Excretive Transport Cause Atypical Intestinal Absorption of Cyclic Phenylalanylserine: Small Intestine Acts as an Interface Between the Body and Ingested Compounds," Research Communications in Molecular Pathology and Pharmacology, 2002, vol. 111, pp. 199-209.

Mizuma et al., "Intestinal Absorption of Stable Cyclic Glycylphenylalanine: Comparison with the Linear Form," J. Pharm. Pharmacol., 1997, vol. 49, pp. 1067-1071.

Molodavkin et al., "[Effect of the novel dipeptide nootropic agent noopept and its metabolite cyclo-L-prolylglycine on the transcallosal evoked potential in the rat brain]," Eksp Klin Farmakol, Mar.-Apr. 2002, vol. 65(2) (Abstract Only Provided).

Monaco et al., "Plasma and cerebrospinal fluid tryptophan in Multiple Sclerosis and Degenerative Diseases," J Neurol Neurosurg Psychiatry, 1979, vol. 42(7), pp. 640-641 (Abstract Only Provided).

Montine et al., "Cerebrospinal Fluid Ab42, Tau, and F2-Isoprostane Concentrations in Patients with Alzheimer Disease, Other Dementias, and in Age-Matched Controls," Acrch Pathol Lab. Med, Apr. 2001, vol. 125, pp. 510-512.

Mori et al., "Alteration by Liquid Protein Diet of TRH and Cyclo(His-Pro) in the Young Rat Brain," Res. Commun Chem Pathol Pharmacol, 1985, vol. 47(1), pp. 157-160 (Abstract Only Provided).

Mori et al., "Brain TRH and Cyclo (His-Pro) and Brain Protein in the Newborn Rat are Altered by Maternal Liquid Protein Feeding," Life Sci, 1983, vol. 32(14), pp. 1607-1612 (Abstract Only Provided).

Mori et al., "Distribution of histidyl-proline diketopiperazine [cyclo (His-Pro)] and thyrotropin-releasing hormone (TRH) in the primate central nervous system," Brain Res, 1982, vol. 245(1), pp. 183-186.

Mori et al., "Histidyl-Proline Diketopiperazine Cyclo (His-Pro): Identification and Characterization in Rat Pancreatic Islets," Biochem Biophys Res Commun, 1983, vol. 115(1), pp. 281-286 (Abstract Only Provided).

Mori et al., "Histidyl-Proline Diketopiperazine cyclo (His-Pro): measurement by radioimmunoassay in human blood in normal subject and in patients with hyper- and hypothyroidism," Biochem Biophys Res Commun, 1982, vol. 109(2), pp. 541-547.

Mori et al., "Regional Dissociation of Histidyl-Proline Diketopiperazine (Cyclo-(His-Pro)) and Thyrotropin-Releasing Hormone (TRH) in the Rat Brain," Brain Research, 1982, vol. 231(2), pp. 451-453 (Abstract Only Provided).

Mori et al., "Specific Radioimmunoassay of Cyclo (His-Pro), a Biologically Active Metabolite of Thyrotropin-Releasing Hormone," Endocrinology, 1981, vol. 108(5), pp. 1995-1997 (Abstract Only Provided).

Mori et al., ["TRH and Cyclo (His-Pro) Concentrations in the Young Rat Brain are Altered by a Liquid Protein Diet]," [Article in Japanese], Nippon Naibunpi Gakkai Zasshi, 1987, vol. 63(7), pp. 846-852 (English Abstract Only).

Morley et al., "Neuropeptides and appetite: contribution of neuropharmacological modeling," Fed. Proc., Nov. 1984, vol. 43(14), pp. 2903-2907 (Abstract Only Provided).

Moss et al. "Th1/Th2 cells in inflammatory disease states: therapeutic implications," Expert Opinion on Biological Therapy, Dec. 2004, vol. 4, No. 12, pp. 1887-1896.

Moss et al., "Kinetics and Mechanism of the Facile Cyclization of Histidyl-Prolineamide to Cyclo (His-Pro) in Aqueous Solution and the Competitive Influence of Human Plasma," J Pharm Pharmacol, 1990, vol. 42(1), pp. 7-12 (Abstract Only Provided).

Murray et al., "Role of α-Synuclein Carboxy-Terminus on Fibril Formation in Vitro," Biochemistry, 2003, vol. 42, pp. 8530-8540.

Nakamura et al., "T-cell mediated inflammatory pathway in osteoarthritis," Osteoarthritis & Cartilage, 1999, vol. 7, pp. 401-402.

Natl Toxicol Program Tech Rep Ser, "NTP toxicology and carcinogenesis studies of methylphenidate hydrochloride (CAS No. 298-59-9) in F344/N rats and B6C3F1 mice (feed studies)," 1995, 439:1-299 Abstract only, PubMed ID 12595924.

Neustadt, "Intra-articular injections for osteoarthritis of the knee," Cleveland Clinic J. Med., 2006, vol. 73(10), pp. 897-911.

Nicholson et al., "NP1-2358 is a tubulin-depolymerizing agent: in-vitro evidence for activity as a tumor vascular-disrupting agent," Anticancer Drugs, Jan. 2006, vol. 17(1), pp. 25-31 (Abstract Only Provided).

Nitecki et al., "A Simple Route to Sterically Pure Kiketopiperazines" J. Org. Chem., 1968, vol. 33(2), pp. 864-866.

O'Connor et al., "Post-proline dipeptidyl-aminopeptidase from synaptosomal membranes of guinea-pig brain," European Journal of Biochemistry, 1986, vol. 154, Iss. 2, pp. 329-335.

(56) References Cited

OTHER PUBLICATIONS

Ostrovskaia et al., "Multicomponent antithrombotic effect of the neuroprotective prolyl dipeptide GVS-111 and its major metabolite cyclo-L-prolylglycine," Eksp Klin Farmakol, Mar.-Apr. 2002, vol. 65(2) (Abstract Only Provided).
Palace et al. "Epilepsy: an autoimmune disease?" Journal of Neurology, Neurosurgery & Psychiatry, Dec. 2000, vol. 69, No. 6, pp. 711-714.
Palacios et al., "Tenidap Decreases IL-8 and Monocyte Chemotactic Peptide-1 (MCP-1) mRNA Expression in the Synovial Tissue of Rabbits with Antigen Arthritis and in Cultured Synovial Cells," Clin. Exp. Immunol., 1998, vol. 111, pp. 588-596.
Pan et al., "Binding of bromine-substituted analogs of methylphenidate to monoamine transporters," Euro J Pharmacol 1994, 264:177-182.
Pandey et al., "Synthetic Peptides Corresponding to a Repetitive Sequence of Malarial Histidine Rich Protein Bind Haem and Inhibit Haemozoin Formation in vitro," Mol Biochem Parasitol, 1997, vol. 90(1), pp. 281-287 (Abstract Only Provided).
Parker et al., "Evidence for the Presence of Immunoreactive Histidyl-Proline Diketopiperazine [Cyclo (His-Pro)] in the Adult Human Brain," Peptides, Nov.-Dec. 1983, vol. 4(6), pp. 879-881 (Abstract Only Provided).
Patrick et al., "Synthesis and pharmacology of hydroxylated metabolites of methylphenidate," J Med Chem 1981, 24(1): 1237-1240.
Pekary et al., "In vitro Production of a TRH-Homologous Peptide and His-Pro Diketopiperazine by Human Semen," J Androl, 1985, vol. 6(6), pp. 379-385 (Abstract Only Provided).
Prakash et al., "Synthesis and Biological Activity of Novel Neuroprotective Diketopiperazines," Bioorganic & Medicinal Chemistry, Sep. 2002, vol. 10(9), pp. 3043-3048.
Prasad et al., "Distribution and Characterization of Cyclo (His-Pro)-Like Immunoreactivity in Human Cerebrospinal Fluid," Biochem Biophys Res Commun, 1986, vol. 136(2), pp. 835-842 (Abstract Only Provided).
Prasad et al., "Distribution and Metabolism of Cyclo (His-Pro): A New Member of the Neuropeptide Family," Peptides, May-Jun. 1982, vol. 3(3), pp. 591-598 (Abstract Only Provided).
Prasad et al., "Increased cerebrospinal fluid cyclo(His-Pro) content in schizophrenia," Neuropeptides, Nov. 1991, vol. 20(3), pp. 187-190.
Prasad et al., "Isolation of cyclo(His-Pro)-like immunoreactivity from Human Urine and Demonstration of its Immunologic, Pharmacologic, and Physico-chemical Identity with the Synthetic Peptide," Biochemistry Int, 1990, vol. 21(3), pp. 425-434 (Abstract Only Provided).
Prasad et al., "Thermoregulation in rats: opposing effects of thyrotropin releasing hormone and its metabolite histidyl-proline diketopiperazine," Biochem Biophys Res. Commun., 1978, vol. 85(4), pp. 1582-187.
Prasad, "Bioactive Cyclic Dipeptides," Peptides, 1995, vol. 16(1), pp. 151-164.
Purves et al. (Eds), Neuroscience, 2001, Sinauer Associates, Inc., 2nd Edition, pp. 75, 367, 400 and 403.
Purves et al., Life: the Science of Biology, 3rd Ed. (1992), p. 376.
Rainbow et al., "Distribution, survival and biological effects in mice of a behaviorally active, enzymatically stable peptide: pharmacokinetics of cyclo(Leu-Gly) and puromycin-induced amnesia," Pharmacol Biochem Behav, May 1979, vol. 10(5), pp. 787-793.
Rainger et al., "Endothelial-Borne Platelet-Activating Factor and Interleukin-8 Rapidly Immobilize Rolling Neutrophils," Am. J. Physiol., 272(Heart Circ. Physiol. 41):H114-H122 (1997).
Rainsford et al., "Effects of 5-Lipoxygenase Inhibitors on Interleukin Production by Human Synovial Tissues in Organ Culture: Comparison with Interleukin-1-Synthesis Inhibitors," J. Pharm. Pharmacol., 48:46-52 (1996).

Ramírez et al., "Platelet Activating Factor Modulates Microvascular Permeability through Nitric Oxide Synthesis," Microvascular Research, 1995, vol. 50, Iss. 2, pp. 223-234.
Reubsaet et al., "Qualitative and Quantitative Aspects of the Degradation of Several Tripeptides Derived from the Antitumor Peptide Antagonist [Arg(6), D-Trp(7,9), MePhe(8)] Substance P[6-11]," J Pharm Biomed Anal 1999, 19(3-4):2.
Rinaldi et al. "Immunological markers in multiple sclerosis: tackling the missing elements," Neurol. Sci., Dec. 2005, vol. 26 Suppl. 4, pp. S215-S217.
Ritalin, available on the World Wide Web at ms.about.com/od/treatment/a/Ritalin.htm, downloaded on May 7, 2006.
Rosenthal et al., "Effects of Arachidonic Acid and Cyclo (His-Pro) on Zinc Transport Across Small Intestine and Muscle Tissues," Life Sci, 2001, vol. 70(3), pp. 337-348 (Abstract Only Provided).
Roth et al., "Platelet-Activating Factor Exerts Mitogenic Activity and Stimulates Expression of Interleukin 6 and Interleukin 8 in Human Lung Fibroblasts via Binding to its Functional Receptor," J. Exp. Med., 1996, vol. 184, pp. 191-201.
Rozans et al., "Palliative Uses of Methylphenidate in Pateints With Cancer: A Review", J. Clin. Oncology, Jan. 1, 2002, vol. 20, No. 1, pp. 335-339.
S. Blazickova et al. "Immunomodulatory Characteristics of Synthetic Cyclic Dipeptides", Int. J. Immunotherapy (1994) 10(3), pp. 89-93.
Sakurada et al., "Antinociceptive activities of synthetic dipeptides in mice." J. Pharm. Pharmacol., 1982, vol. 34, pp. 750-751.
Sakuta et al., "Dual Regulatory Effects of Interferon-α, -β, and -γ on Interleukin-8 Gene Expression by Human Gingival Fibroblasts in Culture Upon Stimulation with Lipopolysaccharide from Prevotella Intermedia, Interleukin-1α, or Tumor Necrosis Factor-α," J. Dent Res., 1998, vol. 77(8), pp. 1597-1605.
Samanta et al., "Crystal Structure of Human Plasma Platelet-activating Factor Acetylhydrolase," J. Biol. Chem., vol. 283(46), Nov. 14, 2008, pp. 31617-31624.
Sammes, "Naturally Occurring 2,5-Dioxopiperazines and Related Compounds," Fortschr. Chem. Org. Naturst., 1975, vol. 32, pp. 51-118.
Sano et al, "Process Research and Development of L-Alanyl-L-Glutamine, a Component of Parenteral Nutrition," Organic Process Research & Development, 2000, vol. 4, pp. 147-152.
Sato et al., "Comparison of the antiociceptive effect between the cyclic dipeptide cyclo[Tyr(Et)-homoarginine] and the linear dipeptide Boc-Tyr(Et)-homoarginine-Ome in rats.," Jpn J Pharmacol, Jan. 1984, vol. 34(1) (Abstract Only Provided).
Scharpe et al., "Peptide Truncation by Dipeptidyl Peptidase IV: A New Pathway for Drug Discovery," Verh K. Acad Geneeskd Belg. 2001, vol. 63(1), pp. 5-32 (Abstract Only Provided).
Schiller et al. "Methlyphenidate Hydrochloride (Ritalin) in Obstructive Pulmonary Disease." Jour Allergy, 1958, vol. 29, No. 2, p. 160-164.
Schlingemann et al., "Role of vascular permeability factor/vascular endothelial growth factor in eye disease," Brit. J. Ophthalmology, vol. 81, 1997, pp. 501-512.
Schwartzbaum et al., "Epidemiology and molecular pathology of glioma," Nature Clinical Practice Neurology, 2006, vol. 2, No. 9, pp. 494-503.
Sepetov et al., "Rearrangement, Racemization and Decomposition of Peptides in Aqueous Solution," Peptide Research, 1991, vol. 4(5), pp. 308-313 (Abstract Only Provided).
Seredenin et al. "Endogenous dipeptide cycloprolylglycine shows selective anxiolytic activity in animals with manifest fear reaction," Bull Exp Biol Med; Apr. 2002; vol. 1333(4) (Abstract Only Provided).
Shaw et al., "Future of early detection of lung cancer: the role of mouse models." Clin Cancer Res., Jul. 1; 11(13 Pt 2): 4999s-5003s, 2005.
Shimazaki et al., "Diketopiperazine Derivatives, a New Series of Platelet-Activating Factor Inhibitors," Chem. Pharm. Bull., 1987, vol. 35(8), pp. 3527-3530.
Shimazaki et al., "Diketopiperazines as a New Class of Platelet-Activating Factor Inhibitors," J. Med. Chem., 1987, vol. 30, pp. 1706-1709.

(56) References Cited

OTHER PUBLICATIONS

Shimazaki et al., "PAF Inhibitory Activity of Diketopiperazines: Structure-Activity Relationships," Lipids, 1991, vol. 26(12), pp. 1175-1178.
Shimi et al., "Isolation of Cairomycins A and C," Antimicrobial Agents and Chemotherapy, Jun. 1981, vol. 19(6), pp. 941-944.
Shukla et al., "Role of Endogenous Cyclo(His-Pro) in Cold-Induced Hypothermia in the Desert Rat (*Mastomys natalensis*)," Peptides; 1994; 15(8):1471-4 (Abstract Only Provided).
Shutov et al., "[Diagnostic Significance of the type of In Vitro Interaction between Blood Lymphocytes and Serotonin in Multiple Sclerosis]," [Article in Russian], Zh Nevrol Psikhiatr Im S S Korsakova, 2002, vol. 102(4), pp. 35-38 (Abstract Only Provided).
Skates et al., "Molecular markers for early detection of renal carcinoma: investigative approach," Clin Cancer Res, Sep. 2004, vol. 10(18 Pt 2), pp. 6296S-6301S.
Smith et al., "Lesson 10, vol. 12—Asthma: Evolving Anti-Inflammatory Therapy," www.chestnet.org/education/pccu/vol12/lesson10.html, pp. 1-8, printed Jul. 20, 2000.
Smith et al., "Recent developments in drug therapy for multiple sclerosis," Mult. Soler., 1999, vol. 5, pp. 110-120.
Smith et al., "Solid-phase synthesis of a library of piperazinediones and diazepinediones via Kaiser oxime resin." Bioorg. Med. Chem., 1998, vol. 8, pp. 2369-2374.
Sollid et al. "Is celiac disease an autoimmune disorder?" Current Opinion in Immunology, Dec. 2005, vol. 17, No. 6, pp. 595-600.
Sollis "Short and novel stereospecific synthesis of trisubstituted 2,5-diketopiperazines," J Org Chem, Jun. 2005, vol. 70(12), pp. 4735-4740 (Abstract Only Provided).
Song et al., "Body weight reduction in rats by oral treatment with zinc plus cyclo-(His-Pro)," Br. J. Pharmacol., Sep. 2009, vol. 158(2), pp. 442-450, Epub May 5, 2009 (Abstract Only Provided).
Song et al., "Raw vegetable food containing high cyclo (his-pro) improved insulin sensitivity and body weight control," Metabolism, Nov. 2005, vol. 54(11), pp. 1480-1489 (Abstract Only Provided).
Song et al., "Synergistic Antidiabetic Activities of Zinc, Cyclo (His-Pro), and Arachidonic Acid," Metabolism 2001 50(1):53-59 (Abstract Only Provided).
Stark et al., "Structures, sensory activity, and dose/response functions of 2,5-diketopiperazines in roasted cocoa nibs (*Theobroma cacao*)." J Agric Food Chem., Sep. 7, 2005, vol. 53(18), pp. 7222-7231 (Abstract Only Provided) PMID: 16131134.
Steiner et al., "Histidyl Proline Diketopiperazine (Cyclo [His-Pro]) in Eating Disorders," Neuropeptides, Oct. 1989, vol. 14(3), pp. 185-189 (Abstract Only Provided).
Strom et al., "Lactobacillus plantarum MiLAB 393 produces the antifungal cyclic dipeptides cyclo(L-Phe-L-Pro) and cyclo(L-Phe-trans-4-OH-L-Pro) and 3-phenyllactic acid.," Appl Environ Microbiol, Sep. 2002, vol. 68(9) (Abstract Only Provided).
Suzuki et al., "Effect of cyclic dipeptides containing histidine on pentobarbital narcosis," J. Pharm. Dyn., May 1981, vol. 4(5), pp. 377-379.
Swigris et al., "Idiopathic Pulmonary Fibrosis: Challenges and Opportunities for the Clinician and Investigator," Chest, 2005, vol. 127, Iss. 1, pp. 275-283.
Takahara et al., "Detection in Human Serum by Radioimmunoassay of Histidyl-Proline Diketopiperazine, a Metabolite of Thyrotropin-Releasing Hormone," J Clinical Endocrinology, 1983, vol. 56(2), pp. 312-319 (Abstract Only Provided).
Tascioglu et al., "Efficacy of intra-articular sodium hyaluronate in the treatment of knee osteoarthritis," Clinical Rheumatology, 2003, vol. 22, Iss. 2, pp. 112-117.
Teo et al., "D-methylphenidate is non-genotoxic in in vitro and in vivo assays," Mutat Res 2003, 537(1): 67-79 Abstract only, PubMed ID 12742508.
Teitel et al., "Rheumatoid arthritis," PubMed Health, reviewed Feb. 2, 2012, available at www.ncbi.nlm.nih.gov/pubmedhealth/PMH0001467/?report=printable, 8 pages.
Teitel et al., "Scleroderma," PubMed Health, reviewed Feb. 2, 2012, available at www.ncbi.nlm.nih.gov/pubmedhealth/PMH0001465/?report=printable, 7 pages.
Teitel et al., "Systemic lupus erythematosus," PubMed Health, reviewed Feb. 2, 2012, available at www.ncbi.nlm.nih.gov/pubmedhealth/PMH0001471/?report=printable, 9 pages.
Thai et al, "Asymmetric synthesis and pharmacology of methylphenidate and its para-substituted derivatives", J Med Chem 1998, 41: 591-601.
Thai et al., "Comparative pharmacokinetics and tissue distribution of the d-enantiomers of para-substituted methylphenidate analogs," Drug Metabolism and Disposition 1999, 27(6): 645-650.
Unal et al., "Cyclo(Gly-Gln) inhibits the cardiorespiratory depression produced by beta-endorphin and morphine," Brain Research, 1997, vol. 747(1), pp. 52-59.
Vara et al., "PI3K/Akt signalling pathway and cancer," Cancer Treatment Reviews, 2004, vol. 30, pp. 193-204.
Vargas et al., "Neuroglial activation and neuroinflammation in the brain of patients with autism", Annal Neurol, Early View (Articles online in advance of print), Wiley InterScience::Article Full Text HTML, available on the World Wide Web at www3.interscience.wile.com/cgi-bin/fulltext/109793289/main.html,ftx_abs, downloaded on Nov. 15, 2004.
Varughese et al., "Crystal structure and conformation of cyclo-L-cystine," Int. J. Pept. Protein Res., vol. 18, Jul. 1981, pp. 88-102.
Vigano et al., "Methylphenidate for the management of somatization in terminal cancer patients," J Pain Symptom Manage 1995, 10(2): 167-170 Abstract only, PubMed ID 7730689.
Vogel et al., "Disseminated tumor cells—Their detection and significance for prognosis of gastrointestinal and pancreatic carcinomas," Virchows Arch, 2001, vol. 439, pp. 109-117.
Walter et al., "Neurohypophyseal hormones, analogs, and fragments: their effect on puromycin-induced amnesia," Proc. Natl. Acad. Sci., Oct. 1975, vol. 72(10), pp. 4180-4184.
Walter et al., "The Cyclized C-Terminal Dipeptide of Arginine Vasopressin: Metabolic Stability and Antagonism of Puromycin-Induced Amnesia," Hormones and Behavior, 1982, vol. 16; p. 234-244.
Wang et al., "A facile pathway to synthesize diketopiperazine derivatives," Tetrahedron Lett, 2002, vol. 43, pp. 865-867.
Wang et al., "Novel inhibitors of plasminogen activator inhibitor-1: development of new templates from diketopiperazines," Bioorg Med Chem Lett, Sep. 2002, vol. 12(17), pp. 2367-2370 (Abstract Only Provided).
Wayment et al., "Effects on methylphenidate analogues on phenethylamine substrates for the striatal dopamine transporter: potential as amphetamine antagonists?" J Neurochem 1999, 72(3): 1266-1274 Abstract only, PubMed ID 10037500.
Weng et al., "Novel CCK-B receptor agonists: diketopiperazine analogues derived for CCK4 bioactive conformation," Regul Pept, Aug. 1996; vol. 65(1) (Abstract Only Provided).
Wennemers et al., "Diketopiperazine Receptors: A Novel Class of Highly Selective Receptors for Binding Small Peptides," Chem. Eur. J., 2001, vol. 7, No. 15, pp. 3342-3347.
Wilber et al., "Endogenous histidyl-proline diketopiperazine [cyclo (His-Pro)]: a potential satiety neuropeptide in normal and genetically obese rodents," Trans Assoc Am Physicians, 1983, vol. 96, pp. 131-136.
Wilber et al., "Histidyl-proline diketopiperazine: a potent and chronic appetite-inhibiting neuropeptide," Trans Assoc. Am Physicians, 1986, vol. 99, pp. 245-249.
Wilkes et al. "Patient Survival after Human Albumin Administration: A Meta-Analysis of Randomized, Controlled Trials." Annals of Internal Medicine, Aug. 2001, vol. 135, No. 3, pp. 149-164.
Wisniewski et al., "Relationship between serum cyclo (His-Pro) concentrations and the nutritional status of HIV-infected patients," South Med. J., Mar. 1994, vol. 87(3), pp. 348-351 (Abstract Only Provided).
Woehlecke et al., "Reversal of breast cancer resistance protein-mediated drug resistance by tryprostatin A.," Int J Cancer; Dec. 2003, vol. 107(5) (Abstract Only Provided).
Wolf et al., "Identification of Cyclo(His-Pro)-Like Immunoreactivity in Human Follicular Fluid: Correlation with Steroid and Peptide

(56) References Cited

OTHER PUBLICATIONS

Hormones," J Soc Gynecol Investigation, 1994, vol. 1(3), pp. 220-224 (Abstract Only Provided).
Wretlind, "The Availability of the Isopropyl Ester of L- and D-Phenylalanine and 3,6-Dibenzyl-2,5-Diketopiperazine form Growth in Rats," Acta phys. Scandinav, May 1953, vol. 30, pp. 97-104.
Wyatt et al., "2,5-Diketopiperazines as potent and selective oxytocin antagonists 1: Identification, stereochemistry and initial SAR," Bioorg Med Chem Lett., May 16, 2005, vol. 15(10), pp. 2579-2582 (Abstract Only Provided) PMID: 15863320.
Yamada et al., "Abundance of Cyclo (His-Pro)-like Immunoreactivity in the Brain of TRH-Deficient Mice," Endocrinology, Jan. 1999, vol. 140(1), pp. 538-541 (Abstract Only Provided).
Yanagisawa et al., "The Subcellular and Organ Distribution and Natural Form of Histidyl-Proline Diketopiperazine in Rat Brain Determined by a Specific Radioimmunoassay," J Biol Chem, Nov. 10, 1980, vol. 255(21), pp. 10290-10294 (Abstract Only Provided).
Yang et al. "Increased hepatic platelet activating factor (PAF) and PAF receptors in carbon tetrachloride induced liver cirrhosis." Gut, Jan. 2004, vol. 53, No. 6, pp. 877-883.
Yi Es, "Hypersensitivity pneumonitis," Crit Rev Clin Lab Sci., Nov. 2002, vol. 39(6), pp. 581-629.
Yoshida et al., "PAF Inhibitors of Microbial Origin," Prog. Biochem. Pharmacol., 1988, vol. 22, pp. 68-80.
Youngblood et al., "Bovine Serum Albumin-GABA-His-Pro-NH2: an Immunogen for Production of Higher Affinity Antisera for TRH," J Neursci Methods, 1983, vol. 9(4), pp. 367-373 (Abstract Only Provided).
Zander et al., "Allogeneic bone marrow transplantation for acute leukemia refractory to induction chemotherapy," Cancer, 1985, vol. 56, Iss. 6, pp. 1374-1379.
Zeng et al., "Synthesis of a small library of diketopiperazines as potential inhibitors of calpain," Bioorg Med Chem Lett, Jun. 2005, vol. 15(12), pp. 3034-3038.
Zhu et al., "Phosphate Prodrugs of PD154075," Bioorganic & Medicinal Chemistry Letters, 2000, vol. 10, Iss. 10, pp. 1121-1124.
Zieve, "Multiple sclerosis," PubMed Health, reviewed Sep. 26, 2011, available at www.ncbi.nlm.nih.gov/pubmedhealth/PMH0001747/?report=printable, 10 pages.
International Search Report for International (PCT) Application No. PCT/US09/45281, mailed Jul. 13, 2009.
Written Opinion for International (PCT) Application No. PCT/US09/45281, mailed Jul. 13, 2009.
International Preliminary Report on Patentability for International (PCT) Application No. PCT/US09/45281, mailed Dec. 9, 2010.
Extended Search Report for European Patent Application No. 09810870.7, dated May 18, 2012 7 pages.
Slater, "Gas-liquid chromatography of 2,5-diketopiperazines as their trifluoroacetyl derivatives," Journal of Chromatography A, 1972, vol. 64, Iss. 1, pp. 166-169.
He et al., "Evidence for a Role of Platelet-Activating Factor (PAF) in the Pathogenesis of Age-Related Macular Degeneration (AMD)", Investigative Ophthalmology & Visual Science, 2007, vol. 48, Iss. 13, 2 pages. (Abstract only).
Sakkas et al., "T Cells and T-Cell Cytokine Transcripts in the Synovial Membrane in Patients with Osteoarthritis", Clinical and Diagnostic Laboratory Immunology, Jul. 1998, vol. 5, No. 4, pp. 430-437.
Yasukawa, "Inflammation in age-related macular degeneration: pathological or physiological?", Expert Review of Ophthalmology, 2009, vol. 4, Iss. 2, pp. 107-112.

\* cited by examiner

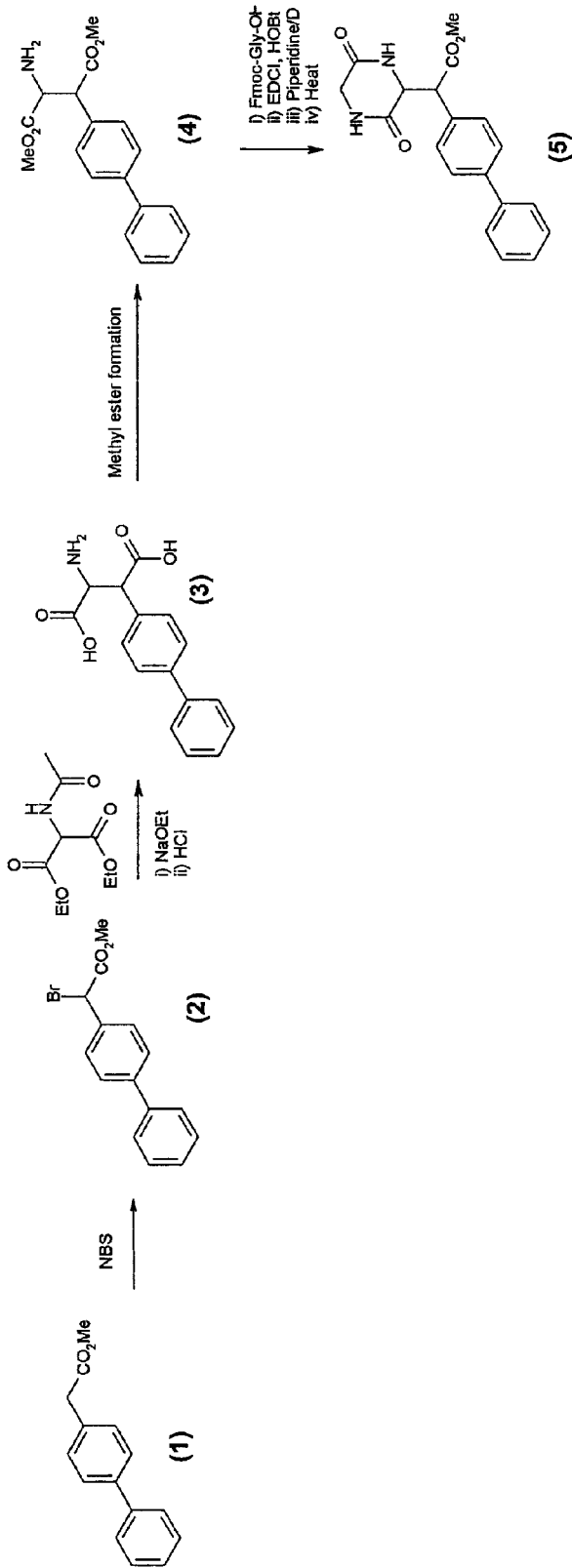

THERAPEUTIC METHODS AND COMPOUNDS

CROSS REFERENCE TO RELATED APPLICATIONS

This application is a divisional of U.S. patent application Ser. No. 13/403,419, filed Feb. 23, 2012, now U.S. Pat. No. 8,871,772, which is a divisional of U.S. patent application Ser. No. 12/472,738, filed May 27, 2009, now U.S. Pat. No. 8,217,047, which claims the benefit of provisional application No. 61/056,379, filed May 27, 2008, the complete disclosures of which are incorporated herein by reference.

FIELD OF THE INVENTION

This invention relates to diketopiperazines and pharmaceutical compositions comprising them as the active ingredient. The invention also relates to the therapeutic treatments that utilize the diketopiperazines, including inhibition of a proliferative disease or condition, inhibition of angiogenesis, treatment of an angiogenic disease or condition, treatment of cancer and precancerous conditions, treatment of a fibrotic disorder, treatment of a viral infection, inhibition of Akt activation, treatment of an Akt-mediated disease or condition, and inhibition of the production, release or both of matrix metalloproteinase-9.

BACKGROUND

Diketopiperazines have been reported to exhibit a variety of biological activities. See, e.g., U.S. Pat. No. 3,941,790 (cancer treatment), U.S. Pat. No. 4,289,759 (immunoregulatory agents), U.S. Pat. No. 4,331,595 (immunoregulatory agents), U.S. Pat. No. 4,940,709 (platelet activating factor (PAF) antagonists), U.S. Pat. No. 5,700,804 (inhibitors of plasminogen activator inhibitor), U.S. Pat. No. 5,750,530 (inhibitors of plasminogen activator inhibitor), U.S. Pat. No. 5,990,112 (inhibitors of metalloproteases), U.S. Pat. No. 6,537,964 (chemosensitizing reversal agents for treatment of multiple drug resistant cancers), U.S. Pat. No. 6,555,543 (inhibitors of PAF, the production and/or release of interleukin 8 (IL-8) and inflammation), and U.S. Pat. No. 6,815,214 (treatment of inflammatory conditions associated with, e.g., cancer and asthma), PCT applications WO 97/36888 (inhibitors of farnesyl-protein transferase), WO 98/9968 (treatment for infections, cancer and other malignant diseases), WO 99/40931 (treatment of central nervous system injury), and WO 04/87162 (agents for treatment of drug resistant cancer), EP application 43219 (immunoregulatory agents), Japanese application 63 290868 (PAF antagonists), Japanese application 31 76478 (immunosuppressive agents), Japanese application 51 63148 (anti-neoplastic agents), Shimazaki et al., *Chem. Pharm. Bull.*, 35(8), 3527-3530 (1987) (PAF antagonists), Shimazaki et al., *J. Med. Chem.*, 30, 1709-1711 (1987) (PAF antagonists), Shimazaki et al., *Lipids*, 26(12), 1175-1178 (1991) (PAF antagonists), Yoshida et al., *Prog. Biochem. Pharmacol.*, 22, 68-80 (1988) (PAF antagonists), Alvarez et al., *J. Antibiotics*, 47(11), 1195-1201 (1994) (inhibitors of calpain).

SUMMARY OF THE INVENTION

The present invention provides a diketopiperazine having the following formula:

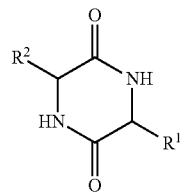

(I)

wherein:
$R^1$ is:
(a) a side chain of an amino acid, wherein the amino acid is glycine, alanine, valine, norvaline, α-aminoisobutyric acid, 2,4-diaminobutyric acid, 2,3-diaminobutyric acid, leucine, isoleucine, norleucine, serine, homoserine, threonine, aspartic acid, asparagine, glutamic acid, glutamine, lysine, hydroxylysine, histidine, arginine, homoarginine, citrulline, phenylalanine, p-aminophenylalanine, tyrosine, tryptophan, thyroxine, cysteine, homocysteine, methionine, penicillamine or ornithine;
(b) —$CH_2$—$CH_2$—$CH_2$— or —$CH_2$—CH(OH)—$CH_2$— and together with the adjacent ring nitrogen forms proline or hydroxyproline; or
(c) a derivative of a side chain of an amino acid, wherein the amino acid is one of those recited in (a), and the derivatized side chain has:
  (i) an —$NH_2$ group replaced by an —$NHR^3$ or —$N(R^3)_2$ group, wherein each $R^3$ may independently be a substituted or unsubstituted alkyl, cycloalkyl, heterocycloalkyl, aryl, alkylaryl, arylalkyl or heteroaryl;
  (ii) an —OH group replaced by an —O—$PO_3H_2$ or —$OR^3$ group, wherein each $R^3$ may independently be a substituted or unsubstituted alkyl, cycloalkyl, heterocycloalkyl, aryl, alkylaryl, arylalkyl or heteroaryl;
  (iii) a —COOH group replaced by a —$COOR^3$ group, wherein each $R^3$ may independently be a substituted or unsubstituted alkyl, cycloalkyl, heterocycloalkyl, aryl, alkylaryl, arylalkyl or heteroaryl;
  (iv) a —COOH group replaced by a —$CON(R^4)_2$ group, wherein each $R^4$ may independently be H or a substituted or unsubstituted alkyl, cycloalkyl, heterocycloalkyl, aryl, alkylaryl, arylalkyl or heteroaryl;
  (v) an —SH group replaced by —S—S—$CH_2$—CH($NH_2$)—COOH or —S—S—$CH_2$—$CH_2$—CH($NH_2$)—COOH;
  (vi) a —$CH_2$— group replaced by a —CH($NH_2$)— or a —CH(OH)— group;
  (vii) a —$CH_3$ group replaced by a —$CH_2$—$NH_2$ or a —$CH_2$—OH group; and/or
  (viii) an H which is attached to a carbon atom replaced by a halogen;
$R^2$ has formula II, III or IV:

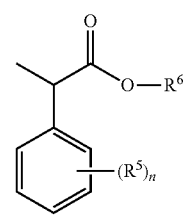

II

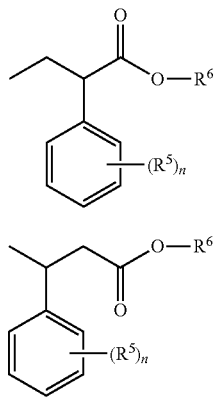

wherein:
each $R^5$ is independently aryl, heteroaryl, alkyl, cycloalkyl, heterocycloalkyl, alkoxy, aryloxy, acyl, carboxyl, hydroxyl, halogen, amino, nitro, sulfo or sulfhydryl, wherein each alkyl is optionally substituted with hydroxyl, amino or sulfhydryl;
n is from 0 to 5; and
$R^6$ is hydrogen or lower alkyl.

The invention also provides a pharmaceutical composition comprising a pharmaceutically-acceptable carrier and an active ingredient, wherein the active ingredient is a diketopiperazine of formula I or a pharmaceutically-acceptable salt or prodrug thereof.

The invention further provides a method of treating a proliferative disease or condition. The method comprises administering to an animal in need thereof an effective amount of a diketopiperazine of formula I or a pharmaceutically-acceptable salt or prodrug thereof.

In addition, the invention provides a method of inhibiting angiogenesis. The method comprises administering to an animal in need thereof an effective amount of a diketopiperazine of formula I or a pharmaceutically-acceptable salt or prodrug thereof.

The invention further provides a method of treating an angiogenic disease or condition. The method comprises administering to an animal in need thereof an effective amount of a diketopiperazine of formula I or a pharmaceutically-acceptable salt or prodrug thereof.

In addition, the invention provides a method of treating a cancer. The method comprises administering to an animal in need thereof an effective amount of a diketopiperazine of formula I or a pharmaceutically-acceptable salt or prodrug thereof.

The invention further provides a method of treating a precancerous condition. The method comprises administering to an animal in need thereof an effective amount of a diketopiperazine of formula I or a pharmaceutically-acceptable salt or prodrug thereof.

The invention also provides a method of treating a fibrotic disorder. The method comprises administering to an animal in need thereof an effective amount of a diketopiperazine of formula I or a pharmaceutically-acceptable salt or prodrug thereof.

In addition, the invention provides a method of treating a viral infection. The method comprises administering to an animal in need thereof an effective amount of a diketopiperazine of formula I or a pharmaceutically-acceptable salt or prodrug thereof.

The invention also provides a method of inhibiting the production, release or both of matrix metalloproteinase-9 (MMP-9) by cells. The method comprises contacting the cells with an effective amount of a diketopiperazine of formula I or a pharmaceutically-acceptable salt or prodrug thereof.

In addition, the invention provides a method of inhibiting the activation (phosphorylation) of Akt by cells. The method comprises contacting the cells with an effective amount of a diketopiperazine of formula I or a pharmaceutically-acceptable salt or prodrug thereof.

The invention further provides a method of treating an Akt-mediated disease or condition. The method comprises administering to an animal in need thereof an effective amount of a diketopiperazine of formula I or a pharmaceutically-acceptable salt or prodrug thereof.

BRIEF DESCRIPTION OF THE DRAWING

FIG. 1: Schematic illustrating the synthesis of biphenyl-4-yl-(3,6-dioxo-piperazin-2-yl)-acetic acid methyl ester (Cpd. 5).

DETAILED DESCRIPTION OF THE PRESENTLY-PREFERRED EMBODIMENTS OF THE INVENTION

The present invention provides diketopiperazines which have the following formula I:

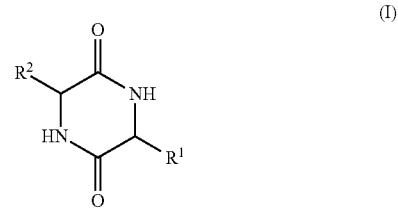

wherein:
$R^1$ is:
(a) a side chain of an amino acid, wherein the amino acid is glycine, alanine, valine, norvaline, α-aminoisobutyric acid, 2,4-diaminobutyric acid, 2,3-diaminobutyric acid, leucine, isoleucine, norleucine, serine, homoserine, threonine, aspartic acid, asparagine, glutamic acid, glutamine, lysine, hydroxylysine, histidine, arginine, homoarginine, citrulline, phenylalanine, p-aminophenylalanine, tyrosine, tryptophan, thyroxine, cysteine, homocysteine, methionine, penicillamine or ornithine;
(b) —CH$_2$—CH$_2$—CH$_2$— or —CH$_2$—CH(OH)—CH$_2$— and together with the adjacent ring nitrogen forms proline or hydroxyproline; or
(c) a derivative of a side chain of an amino acid, wherein the amino acid is one of those recited in (a), and the derivatized side chain has:
(i) an —NH$_2$ group replaced by an —NHR$^3$ or —N(R$^3$)$_2$ group, wherein each R$^3$ may independently be a substituted or unsubstituted alkyl, cycloalkyl, heterocycloalkyl, aryl, alkylaryl, arylalkyl or heteroaryl;
(ii) an —OH group replaced by an —O—PO$_3$H$_2$ or —OR$^3$ group, wherein each R$^3$ may independently be a substituted or unsubstituted alkyl, cycloalkyl, heterocycloalkyl, aryl, alkylaryl, arylalkyl or heteroaryl;

(iii) a —COOH group replaced by a —COOR³ group, wherein each R³ may independently be a substituted or unsubstituted alkyl, cycloalkyl, heterocycloalkyl, aryl, alkylaryl, arylalkyl or heteroaryl;

(iv) a —COOH group replaced by a —CON(R⁴)₂ group, wherein each R⁴ may independently be H or a substituted or unsubstituted alkyl, cycloalkyl, heterocycloalkyl, aryl, alkylaryl, arylalkyl or heteroaryl;

(v) an —SH group replaced by —S—S—CH₂—CH(NH₂)—COOH or —S—S—CH₂—CH₂—CH(NH₂)—COOH;

(vi) a —CH₂— group replaced by a —CH(NH₂)— or a —CH(OH)— group;

(vii) a —CH₃ group replaced by a —CH₂—NH₂ or a —CH₂—OH group; and/or (viii) an H which is attached to a carbon atom replaced by a halogen;

R² has formula II, III or IV:

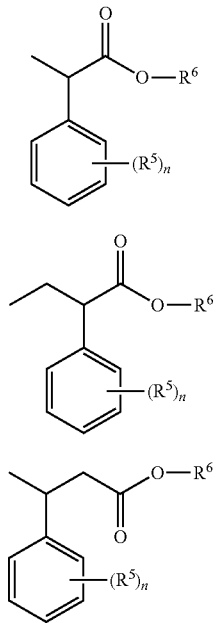

wherein:

each R⁵ is independently aryl, heteroaryl, alkyl, cycloalkyl, heterocycloalkyl, alkoxy, aryloxy, acyl, carboxyl, hydroxyl, halogen, amino, nitro, sulfo or sulfhydryl, wherein each alkyl is optionally substituted with hydroxyl, amino or sulfhydryl;

n is from 0 to 5; and

R⁶ is hydrogen or lower alkyl.

Preferably, R¹ is a side chain of glycine, alanine, valine, norvaline, α-aminoisobutyric acid, 2,4-diaminobutyric acid, 2,3-diaminobutyric acid, leucine, isoleucine, norleucine, serine, homoserine, threonine, aspartic acid, asparagine, glutamic acid, glutamine, lysine, hydroxylysine, histidine, arginine, homoarginine, citrulline, phenylalanine, p-aminophenylalanine, tyrosine, tryptophan, thyroxine or ornithine, or is a derivative of one of these side chains.

More preferably, R¹ is a side chain of glycine, alanine, valine, norvaline, α-aminoisobutyric acid, 2,4-diaminobutyric acid, 2,3-diaminobutyric acid, leucine, isoleucine, norleucine, serine, homoserine, threonine, aspartic acid, aspara-gine, glutamic acid, glutamine, lysine, hydroxylysine, arginine, homoarginine, citrulline or ornithine, or is a derivative of one of these chains.

Even more preferably, R¹ is the side chain of glycine, alanine, valine, leucine or isoleucine, more preferably glycine or alanine, most preferably glycine.

Preferably, R² has formula II or III, most preferably II.

R⁵ is preferably aryl, heteroaryl or aryloxy. More preferably R⁵ is aryl or aryloxy. Most preferably R⁵ is phenyl or phenoxy.

Preferably, n is 1-3. Most preferably n is 1. When n is 1, R⁵ is preferably in the 4 (para) position on the ring.

R⁶ is preferably methyl.

The most highly preferred compound is biphenyl-4-yl-(3,6-dioxo-piperazin-2-yl)-acetic acid methyl ester (referred to as Cpd. 5 herein).

By "replaced" is meant that, with reference to the formula of an amino acid side chain, the specified group is replaced by the other specified group. For instance, the formula of the isoleucine side chain is —CH(CH₃)—CH₂—CH₃. If the terminal —CH₃ group is replaced with a —CH₂—OH group, then the formula of the resulting derivatized isoleucine side chain would be —CH(CH₃)—CH₂—CH₂—OH. As another example, the formula of the alanine side chain is —CH₃. If one of the hydrogen atoms is replaced by a chlorine atom, then the resulting derivatized alanine side chain would be —CH₂—Cl. Note that the side chain of glycine is —H and, if this H is replaced by a chlorine (or other halogen) atom, the resulting side chain will —Cl, with the chlorine atom attached to the ring carbon (e.g., R¹=—Cl)

By "side chain" of an amino acid is meant that portion of the amino acid attached to the common NH₂—CH—COOH backbone of all of the amino acids listed above. For instance, the side chain of glycine is —H, the side chain of alanine is —CH₃, and the side chain of serine is —CH₂OH.

By "acyl" is meant a moiety of the formula —C(O)R⁷, wherein R⁷ is hydrogen, alkyl, cycloalkyl or aryl.

By "alkoxy" is meant a moiety of the formula —OR⁸ wherein R⁸ is alkyl. An example of an alkoxy group is methoxy (—O—CH₃).

By "alkyl" is meant a monovalent saturated straight-chain or branched hydrocarbon containing 1-10 carbon atoms, preferably 1-8, carbon atoms. Each alkyl may, optionally, be substituted with one or more amino, hydroxyl or sulfhydryl groups. "Lower alkyl" means a monovalent saturated straight-chain or branched hydrocarbon containing 1-6 carbon atoms.

By "alkylaryl" is meant a lower alkyl having an H replaced by an aryl (e.g., —CH₂—C₆H₅ or —CH₃CH(C₆H₅)CH₃).

By "amino" is meant a moiety of the formula —NR⁹R¹⁰, wherein each R⁹ and R¹⁰ is independently H or lower alkyl.

By "aryl" is meant a monovalent mono-, bi- or tricyclic aromatic hydrocarbon moiety having 6-14 ring carbon atoms. Preferred is phenyl.

By "aryloxy" is meant a moiety of the formula —OR¹¹ wherein R¹¹ is an aryl. Preferred is phenoxy.

By "arylalkyl" is meant an aryl having an H replaced by a lower alkyl (e.g., —C₆H₄—CH₃).

By "carboxyl" is meant —COOH.

By "cycloalkyl" is meant a saturated monovalent mono- or bicyclic hydrocarbon moiety having three to ten ring carbon atoms. Preferably, the cycloalkyl contains 4-8 ring carbon atoms. The most preferred cycloalkyl is cyclohexyl.

By "halogen" is meant chlorine, fluorine, bromine or iodine. Preferred is chlorine or bromine.

By "heteroaryl" is meant an aryl having at least one, preferably no more than three, of the ring carbon atoms replaced by an O, S or N.

By "heterocycloalkyl" is meant a cycloalkyl having at least one, preferably no more than three, of the ring carbon atoms replaced by an O, S or N.

By "hydroxyl" is meant —OH.

By "nitro" is meant —$NO_2$.

By "substituted" is meant that the moiety is substituted with one or more substituents selected from the following group: —OH, $NH_2$, —SH, —COOH and/or a halogen atom.

By "sulfhydryl" is meant —SH.

By "sulfo" is meant —$SO_3H$ or $SO_2$.

Methods of making diketopiperazines are well known in the art, and these methods may be employed to synthesize the diketopiperazines of the invention. See, e.g., U.S. Pat. Nos. 5,817,751, 5,932,579, 5,990,112, 6,395,774, 6,555,543 and 7,288,345, US Patent Application Publications Numbers 2004/00132738 and 2004/0024180, PCT applications WO 96/00391 and WO 97/48685, Smith et al., *Bioorg. Med. Chem. Letters*, 8, 2369-2374 (1998), Prakash et al., *Bioorg. Med. Chem. Letters*, 10, 3034-3048 (2002), Fischer, *J. Peptide Sci.*, 9, 9-35 (2003), and Zeng et al., *Bioorg. Med. Chem. Letters*, 15, 3034-3038 (2005). The complete disclosures of these references are incorporated herein by reference as exemplary methods of synthesizing diketopiperazines of the present invention.

For instance, diketopiperazines can be prepared by first synthesizing dipeptides. The dipeptides can be synthesized by methods well known in the art using L-amino acids, D-amino acids or a combination of D- and L-amino acids. Preferred are solid-phase peptide synthetic methods. Of course, dipeptides are also available commercially from numerous sources, including DMI Synthesis Ltd., Cardiff, UK (custom synthesis), Sigma-Aldrich, St. Louis, Mo. (primarily custom synthesis), Phoenix Pharmaceuticals, Inc., Belmont, Calif. (custom synthesis), Fisher Scientific (custom synthesis) and Advanced ChemTech, Louisville, Ky. Once the dipeptide is synthesized or purchased, it is cyclized to form a diketopiperazine. This can be accomplished by a variety of techniques.

For example, U.S. Patent Application Publication Number 2004/0024180 describes a method of cyclizing dipeptides. Briefly, the dipeptide is heated in an organic solvent while removing water by distillation. Preferably, the organic solvent is a low-boiling azeotrope with water, such as acetonitrile, allyl alcohol, benzene, benzyl alcohol, n-butanol, 2-butanol, t-butanol, acetic acid butylester, carbon tetrachloride, chlorobenzene chloroform, cyclohexane, 1,2-dichlorethane, diethylacetal, dimethylacetal, acetic acid ethylester, heptane, methylisobutylketone, 3-pentanol, toluene and xylene. The temperature depends on the reaction speed at which the cyclization takes place and on the type of azeotroping agent used. The reaction is preferably carried out at 50-200° C., more preferably 80-150° C. The pH range in which cyclization takes place can be easily determined by the person skilled in the art. It will advantageously be pH 2-9, preferably pH 3-7.

When one or both of the amino acids of the dipeptide has, or is derivatized to have, a carboxyl group on its side chain (e.g., aspartic acid or glutamic acid), the dipeptide is preferably cyclized as described in U.S. Pat. No. 6,555,543. Briefly, the dipeptide, with the side-chain carboxyl still protected, is heated under neutral conditions. Typically, the dipeptide will be heated at from about 80° C. to about 180° C., preferably at about 120° C. The solvent will be a neutral solvent. For instance, the solvent may comprise an alcohol (such as butanol, methanol, ethanol, and higher alcohols, but not phenol) and an azeotropic co-solvent (such as toluene, benzene, or xylene). Preferably, the alcohol is butan-2-ol, and the azeotropic co-solvent is toluene. The heating is continued until the reaction is complete, and such times can be determined empirically. Typically, the dipeptide will be cyclized by refluxing it for about 8-24 hours, preferably about 18 hours. Finally, the protecting group is removed from the diketopiperazine. In doing so, the use of strong acids (mineral acids, such as sulfuric or hydrochloric acids), strong bases (alkaline bases, such as potassium hydroxide or sodium hydroxide), and strong reducing agents (e.g., lithium aluminum hydride) should be avoided, in order to maintain the chirality of the final compound.

Dipeptides made on solid phase resins can be cyclized and released from the resin in one step. See, e.g., U.S. Pat. No. 5,817,751. For instance, the resin having an N-alkylated dipeptide attached is suspended in toluene or toluene/ethanol in the presence of acetic acid (e.g., 1%) or triethylamine (e.g., 4%). Typically, basic cyclization conditions are preferred for their faster cyclization times.

Other methods of cyclizing dipeptides and of making diketopiperazines are known in the art and can be used in the preparation of diketopiperazines useful in the practice of the invention. See, e.g., those references listed above.

To prepare the diketopiperazine of formula I wherein the amino acid side chains are derivatized, amino acid derivatives can be used in the synthesis of the dipeptides, the dipeptides can be derivatized and/or the diketopiperazines can be derivatized, as is known in the art. See, e.g., those references cited above. Also see U.S. Pat. No. 5,589,501, U.S. Patent Appl. Pub. No. 2005/0215468, EP Patent Application No. 1,445,323, Chang et al., *J. Med. Chem.*, 16(11): 1277-1280 (1973). The complete disclosures of these references are incorporated herein by reference, as exemplary methods of making amino acid derivatives with $R^2$ side chains (e.g., aspartic acid and glutamic acid derivatives).

The diketopiperazines of formula I include all possible stereoisomers that can be obtained by varying the configuration of the individual chiral centers, axes or surfaces. In other words, the diketopiperazines of formula I include all possible diastereomers, as well as all optical isomers (enantiomers).

When a diketopiperazine of formula I contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four volume compendium *Optical Resolution Procedures for Chemical Compounds*: Optical Resolution Information Center, Manhattan College, Riverdale, N.Y., and in *Enantiomers, Racemates and Resolutions*, Jean Jacques, Andre Collet and Samuel H. Wilen; John Wiley & Sons, Inc., New York, 1981, which are incorporated herein in their entirety. Basically, the resolution of the compounds is based on the differences in the physical properties of diastereomers by attachment, either chemically or enzymatically, of an enantiomerically pure moiety, resulting in forms that are separable by fractional crystallization, distillation or chromatography.

The pharmaceutically-acceptable salts of the diketopiperazines of formula I may also be used in the practice of the invention. Pharmaceutically-acceptable salts include conventional non-toxic salts, such as salts derived from inorganic acids (such as hydrochloric, hydrobromic, sulfuric, phosphoric, nitric, and the like), organic acids (such as acetic, propionic, succinic, glycolic, stearic, lactic, malic, tartaric, citric, glutamic, aspartic, benzoic, salicylic, oxalic, ascorbic acid, and the like) or bases (such as the hydroxide, carbonate or bicarbonate of a pharmaceutically-acceptable metal cation or organic cations derived from N,N-dibenzylethylenediamine, D-glucosamine, or ethylenediamine). The salts are prepared in a conventional manner, e.g., by neutralizing the free base form of the compound with an acid.

"Prodrug" means any compound which releases an active parent drug according to formula I in vivo when such prodrug is administered to an animal. Prodrugs of a diketopiperazine of formula I are prepared by modifying one or more functional group(s) present in the diketopiperazine of formula I in such a way that the modification(s) may be cleaved in vivo to release the parent drug (i.e., the diketopiperazine of formula I). Prodrugs include diketopiperazines of formula I wherein a hydroxy, amino, or sulfhydryl group in a compound of formula I is bonded to any group that may be cleaved in vivo to generate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of formula I, and the like.

As noted above, the invention provides a method of treating a proliferative disease or condition. A proliferative disease or condition is a disease or condition causing, caused by, involving, or exacerbated by, proliferation of cells. Specific proliferative diseases and conditions that can be treated with a diketopiperazine of formula I or a pharmaceutically-acceptable salt or prodrug thereof, include blood vessel proliferative disorders, cancer, mesangial cell proliferation disorders, fibrotic disorders and hyperproliferative skin disorders.

Blood vessel proliferative disorders include angiogenic diseases and conditions. An angiogenic disease or condition is a disease or condition causing, caused by, involving, exacerbated by, or dependent on angiogenesis. Angiogenesis is the process of new blood vessel formation in the body. Angiogenesis is also used herein to mean the same as, or to include, neovascularization, vascularization, arterialization and vasculogenesis.

A diketopiperazine of the invention or a pharmaceutically-acceptable salt or prodrug thereof will inhibit angiogenesis and can be used to treat an angiogenic disease or condition. Specific angiogenic diseases and conditions treatable according to the invention include neoplastic diseases (e.g., tumors (e.g., tumors of the bladder, brain, breast, cervix, colon, rectum, kidney, lung, ovary, pancreas, prostate, stomach and uterus) and tumor metastasis), benign tumors (e.g., hemangiomas, acoustic neuromas, neurofibromas, trachomas, and pyrogenic granulomas), hypertrophy (e.g., cardiac hypertrophy induced by thyroid hormone), connective tissue disorders (e.g., arthritis and atherosclerosis), psoriasis, ocular angiogenic diseases (e.g., diabetic retinopathy, retinopathy of prematurity, macular degeneration, corneal graft rejection, neovascular glaucoma, retrolental fibroplasia, and rubeosis), cardiovascular diseases, cerebral vascular diseases, endometriosis, polyposis, obesity, diabetes-associated diseases, hemophiliac joints, inflammation and autoimmunity. The diketopiperazines of the invention will be particularly useful for the treatment of neoplastic diseases and ocular angiogenic diseases (especially diabetic retinopathy and macular degeneration). The diketopiperazines of the invention can also be used to inhibit the vascularization required for embryo implantation, thereby providing a method of birth control.

The invention also provides a method of treating a cancer or a precancerous condition. Cancers treatable with a diketopiperazine of formula I, or a pharmaceutically-acceptable salt or prodrug thereof, include carcinomas, sarcomas, osteoscarcomas, lymphomas, leukemias, hematologic malignancies, cancer syndromes, malignant tumors, and metastases. Specific cancers treatable according to the invention include brain cancers, head and neck cancers, breast cancers, cardiac cancers, ovarian cancers, cervical cancers, endometrial cancers, urogenital cancers, prostate cancers, gastric cancers, colorectal cancers, pancreatic cancers, bladder cancers, thyroid cancers, hepatic cancers, lung cancers, bone cancers, skin cancers and Kaposi's sarcomas. Specific cancer syndromes treatable according to the invention include Bannayan-Zonana syndrome, Cowden disease and Lhermitte-Duclos disease. Specific malignant tumors treatable according to the invention include malignant tumors of the bladder, bone, brain, breast, cervix, colon, heart, kidney, liver, lung, lymph tissue, ovary, pancreas, prostate, rectum, skin, stomach, thyroid, urogenital and uterus.

The diketopiperazines of the invention are especially useful for the treatment of breast cancer and melanoma and for the treatment of metastases. The diketopiperazines of the invention are also especially useful for the treatment of malignant brain tumors, including primary tumors and metastatic (secondary) tumors. About half of all primary brain tumors are gliomas. Gliomas include astrocytomas (e.g., pilocytic astrocytomas, low-grade astrocytomas, anaplastic (high-grade) astrocytomas and glioblastomas multiforme), brain stem gliomas ependymomas, ganglioneuromas, juvenile pilocytic gliomas, mixed gliomas, oligodendrogliomas and optic nerve gliomas. Glioblastomas are the most common malignant brain tumors in adults and are probably the most resistant of all cancers to treatment. Other primary brain tumors include carniopharyngiomas, medulloblastomas, pineal tumors, pituitary adenomas, primitive neuroectodermal tumors and vascular tumors. Metastatic brain tumors are tumors that have spread to the brain from another part of the body. The most common cancers that metastasize to the brain include breast, melanoma and lung cancers. Metastatic brain tumors are the most common form of brain tumor and considerably outnumber primary brain tumors.

Precancerous conditions treatable with a diketopiperazine of formula I, or a pharmaceutically-acceptable salt or prodrug thereof, include myelodysplastic syndrome, aplastic anemia, cervical lesions, skin nevi (pre-melanoma), prostatic intraepithelial (intraductal) neoplasia, ductal carcinoma in situ, *Helicobacter pylori* infections of the stomach, colon polyps, severe hepatitis or cirrhosis (especially virally-induced hepatitis) of the liver, and other premalignant conditions that can progress to cancer.

Mesangial cell proliferative disorders refer to disorders brought about by abnormal proliferation of mesangial cells. Mesangial cell proliferative disorders include renal diseases, such as glomerulonephritis, diabetic nephropathy, malignant nephrosclerosis, thrombotic microangiopathy syndromes and glomerulopathies.

Fibrotic disorders are diseases or conditions causing, caused by, involving or exacerbated by the abnormal formation of extracellular matrices, unwanted or excessive fibrosis, or both. Fibrotic disorders can occur in, for instance, skin, liver, kidney, heart or lung tissue. Fibrotic disorders include scarring (e.g., keloid formation and hypertrophic scars), scleroderma, kidney fibrosis (e.g., glomerular sclerosis or renal tubulointerstitial fibrosis), pulmonary fibrosis (including idiopathic pulmonary fibrosis), cardiac fibrosis, chemotherapy/radiation-induced lung fibrosis, pancreatitis, atherosclerosis, restenosis, inflammatory bowel disease, Crohn's disease, arthritis, cancer (e.g., invasive breast cancer, stromal rich mammary tumors, dermatofibromas, angiolipoma and angioleiomyoma), fascitis, general fibrosis syndrome (characterized by replacement of normal muscle tissue by fibrous tissue in varying degrees), liver fibrosis (e.g., hepatic cirrhosis), acute fibrosis (e.g., in response to various forms of trauma, including accidental injuries, infections, surgery, burns, radiation or chemotherapy treatment), macular degeneration and diabetic retinopathy.

Hyperproliferative skin disorders include psoriasis, skin cancer and epidermal hyperproliferation.

The diketopiperazines of the invention, or a pharmaceutically-acceptable salt or prodrug thereof, can also be used to treat viral infections. Specific viral infections treatable according to the invention include infections caused by hepatitis B virus, hepatitis C virus, rubella virus, human immunodeficiency virus (HIV), human herpesvirus 4 (Epstein-Barr virus), human herpesvirus 5 (human cytomegalovirus or HCMV), human herpesvirus 8 (Kaposi's sarcoma-associated herpesvirus or KSHV), human papillomarvirus (HPV), polyomaviruses, human respiratory syncytial virus (RSV), adenovirus and influenza virus.

The invention also provides a method of inhibiting the production, release or both of matrix metalloproteinase-9 (MMP-9) by cells. The method comprises contacting the cells with an effective amount of a diketopiperazine of formula I or a pharmaceutically-acceptable salt or prodrug thereof. The cells can be contacted with the diketopiperazine by any method known in the art. In particular, the cells can be contacted with the diketopiperazine in vivo by administering an effective amount of the diketopiperazine to an animal.

Cells that produce and/or release MMP-9 include those cells found in or around a tumor. Such cells include the tumor cells themselves, stromal cells, eosinophils, macrophages, neutrophils and endothelial cells. See Thiennu H. Vu and Zena Werb, "Gelatinase B: Structure, Regulation, and Function," pages 115-148, in *Matrix Metalloproteinases* (Academic Press, Editors William C. Parks and Robert P. Mecham, 1998). Cells that produce and/or release MMP-9 also include cells involved in inflammation. See, e.g, Id., Solakivi et al., *Lipids in Health and Disease,* 8(11) (Epub Mar. 30, 2009), Lu et al., *J. Leukocyte Biol.,* 78:259-265 (2005) and Amin et al., *Genes Cells,* 8:515-523 (2003).

The invention also provides a method of inhibiting the activation of Akt by cells. The method comprises contacting the cells with an effective amount of a diketopiperazine of formula I or a pharmaceutically-acceptable salt or prodrug thereof. The cells can be contacted with the diketopiperazine by any method known in the art. In particular, the cells can be contacted with the diketopiperazine in vivo by administering an effective amount of the diketopiperazine to an animal.

Protein kinases are involved in the signal transduction pathways linking growth factors, hormones and other cell regulation molecules to cell growth, survival and metabolism. One such protein kinase is Akt kinase. Akt kinase, also known as protein kinase B, is a serine/threonine kinase that plays a central role in promoting the proliferation and survival of a wide range of cell types, thereby protecting cells from apoptosis. A number of protein kinases and phosphatases regulate the activity of Akt. For instance, activation of Akt is mediated by phosphatidylinositol 3'—OH kinase (PI3 kinase or PI3K). Activated PI3K produces phosphatidylinositol-3,4,5-triphosphate $(PI(3,4,5)P_3)$ at the inner side of the plasma membrane. The increase in $PI(3,4,5)P_3$ recruits Akt to the inner membrane, where it is activated. Akt can also be activated by growth signals that are independent of PI3K. Full activation of Akt requires phosphorylation at two sites by two different kinases.

Activated Akt modulates the function of numerous substrates involved in the regulation of cell proliferation, growth and survival, and of cell cycle entry and progression, and activated Akt is involved in the regulation of numerous cellular processes, including transcription, differentiation, metabolism, apoptosis, migration, metastasis, angiogenesis and fibrosis. As a consequence, Akt plays a role in numerous diseases and conditions.

In particular, Akt is known to play a critical role in cancer. Activation of Akt contributes to tumorigenesis in many types of tissues, including breast, ovarian, brain, prostate, skin and lymph tissues. Elevated levels of activated Akt have been detected in a variety of cancers, including ovarian, breast, prostate, pancreatic, gastric, colorectal, brain, thyroid, lung, skin, leukemia and undifferentiated tumors (suggesting that Akt may be associated with tumor aggressiveness and progression). In addition, it has been found that Akt is constitutively active in a wide array of cancers. The phosphatase PTEN is a critical negative regulator of Akt, and its function is lost in many cancers, including breast and prostate carcinomas, glioblastomas and several cancer syndromes, including Bannayan-Zonana syndrome, Cowden disease and Lhermitte-Duclos disease. Tumor cells without functional PTEN show elevated levels of activated Akt. Cancer treatment by chemotherapy and gamma-irradiation kills target cells primarily by induction of apoptosis, and the anti-apoptotic effects of activated Akt contribute to both chemotherapeutic resistance and radiation resistance. Activated Akt also contributes to tumor invasiveness and metastasis. Akt activation is associated with increased expression and secretion of matrix metalloproteases MMP-9 and MMP-2, and Akt has the ability to up-regulate angiogenesis, both of which also contribute to tumor survival.

Akt also plays a role in the life cycle of viruses. See, e.g., Cooray, *J. Gen. Virol.,* 85:1065-1076 (2004) and PCT application WO 2007/149730. In particular, inhibition of apoptosis has become recognized as an important contributory factor in virus survival. Apoptotic inhibition contributes to the establishment of latent and chronic infections and has been implicated in viral oncogenesis. Virus modulation of the PI3K/Akt pathway provides an alternative to the expression of viral oncogenes or the direct inhibition of pro-apoptotic proteins. It has become evident that many viruses require upregulation of this pathway to sustain long-term infections and it is modulated, in some cases, by specific viral products to create an environment favorable for cellular transformation. In other cases, PI3K/Akt signaling simply helps to create an environment favorable for virus replication and virion assembly.

Akt plays a role in angiogenesis and fibrosis. Angiogenesis and fibrosis are key components in development, growth, wound healing and regeneration. Activation of Akt is sufficient to induce angiogenesis, and activated Akt plays an important role in several of the processes involved in angiogenesis. See, e.g., Jiang and Liu, *Current Cancer Drug Targets,* 8:19-26 (2008); Sheng et al., *J. Cell. Physiol.,* 218:451-454 (2009). Activation of the Akt pathway results in the production of connective tissue growth factor (CTGF). CTGF is a potent growth factor that has been shown to play a role in fibroblast proliferation, cell adhesion and the stimulation of extracellular matrix (ECM) production, and CTGF is a potent activator of fibrosis. Accordingly, Akt is a target of choice for anti-angiogenesis therapy for cancer and other angiogenic diseases and conditions and for treating fibrotic disorders.

Due to its pivotal role in controlling cell proliferation, apopotosis and cell migration, Akt is the master regulator of the proliferative/migratory response of vessel wall cells to injury. PCT application WO 03/032809. Accordingly, restenosis of vessels after angioplasty and narrowing of implanted blood vessels (such as arteries, veins, vascular grafts and conduits) following implantation can be prevented or reduced by inhibiting Akt activity in the cells of the vessel. Id. The Akt inhibitor is preferably administered locally to the blood vessel (such as through a catheter or by being provided as part of a coating on a stent). Id.

Akt activation has also been reported to play a role in inflammation and autoimmunity. See, e.g, Ottonello et al., *Br. J. Pharmacol.*, (Mar. 25, 2009) (Epub ahead of print) (PMID 19338579), Solakivi et al., *Lipids in Health and Disease*, 8(11) (Epub Mar. 30, 2009), Rane et al., *Front. Biosci.*, 14:2400-2412 (2009), Baker et al., *J. Immunol.*, 182(6):3819-3826 (2009), Takeshima et al., *BMC Microbiol.*, 9:36 (2009), Patel et al., *Immunol. Res.*, 31(1):47-55 (2005), Lu et al., *J. Leukocyte Biol.*, 78:259-265 (2005), and Amin et al., *Genes Cells*, 8:515-523 (2003).

For general background on Akt and its involvement in various diseases and conditions, see, e.g., U.S. Pat. Nos. 7,175,844, 7,220,539 and 7,378,403, U.S. Pub. Patent Appl. No., 2008/0009507, PCT applications numbers WO 2009/032651, WO 2009/009793, WO 2007/149730, WO 2004/086038 and WO 03/032809, Russo et al., *Int. J. Oncol.*, 34(6):1481-1489 (June 2009) (abstract, PMID 19424565, full article in process), Sheng et al., *J. Cell. Physiol.*, 218:451-454 (2009), Ottonello et al., *Br. J. Pharmacol.*, (Mar. 25, 2009) (Epub ahead of print) (PMID 19338579), Solakivi et al., *Lipids in Health and Disease*, 8(11) (Epub Mar. 30, 2009), Rane et al., *Front. Biosci.*, 14:2400-2412 (2009), Baker et al., *J. Immunol.*, 182(6):3819-3826 (2009), Takeshima et al., *BMC Microbiol.*, 9:36 (2009), Sinnberg et al., *J. Invest. Dermatol.*, PMID 19078992, abstract of article Epub Dec. 11, 2008, Cho and Park, *Int. J. Mol. Sci.*, 9(11):2217-2230 (November 2008), Qiao et al., *Cell Cycle*, 7(19):2991-2996 (Epub Oct. 13, 2008), Jiang and Liu, *Current Cancer Drug Targets*, 8:19-26 (2008), Dida et al., *Experimental Hematology*, 36:1343-1353 (2008), Ji et al., *Recent Pat. Biotechnol.*, 2(3):218-226 (2008), Wang et al., *J. Neuroscience*, 26(22):5996-6003 (2006), Chen et al., *Current Medicinal Chemistry—Anti-Cancer Agents*, 9(6):575-589 (November 2005), Kim et al., *Endocrinology*, 146(10): 4456-4463 (2005), Patel et al., *Immunol. Res.*, 31(1):47-55 (2005), Lu et al., *J. Leukocyte Biol.*, 78:259-265 (2005), Cooray, *J. Gen. Virol.*, 85:1065-1076 (2004), and Amin et al., *Genes Cells*, 8:515-523 (2003), the complete disclosures of all of which are incorporated herein by reference.

The diketopiperazines of the present invention, or a pharmaceutically-acceptable salt or prodrug thereof, can be used to treat an Akt-mediated disease or condition. An Akt-mediated disease or condition is a disease or condition causing, caused by, involving, or exacerbated by, activation of Akt. Akt-mediated diseases and conditions include proliferative diseases and conditions, angiogenic diseases and conditions, cancer, fibrotic disorders, restenosis, viral infections, inflammation and autoimmunity.

While not wishing to be bound by any theory, it is presently believed that it is the $R^2$ side chain of the diketopiperazines of formula I that is primarily responsible for their activity. Further, it is presently believed that optimum activity is obtained when $R^2$ has formula II, $R^5$ is aryl, heteroaryl or aryloxy, n is 1 and $R^6$ is methyl. Preferably, $R^5$ is aryl or aryloxy. More preferably, $R^5$ is phenyl or phenoxy, most preferably phenyl. Also, preferably, $R^5$ is in the 4 (para) position on the ring.

It is to be understood that the scope of this invention encompasses not only the use of the diketopiperazines of formula I themselves, but also the pharmaceutically-acceptable salts and prodrugs thereof. In addition, the present invention contemplates the use of the isomers of the diketopiperazines of formula I, and of the pharmaceutically-acceptable salts and prodrugs thereof, including pure isomers and various mixtures of isomers.

"Inhibit" or "inhibiting" is used herein to mean to reduce (wholly or partially) or to prevent.

"Treat," "treating" or "treatment" is used herein to mean to reduce (wholly or partially) the symptoms, duration or severity of a disease or condition, including curing the disease, or to prevent, or reduce the incidence of, the disease or condition (i.e., to cause the symptoms of the disease or condition not to develop in an animal that may be exposed or predisposed to the disease or condition, but does not yet experience or display symptoms of the disease or condition).

By "effective amount" is meant the amount of a compound that, when administered to an animal for treating a disease or condition or for causing an effect is sufficient to do so. The "effective amount" can and will most likely vary depending on the compound, the disease or condition and its severity, or the effect sought to be caused, and the age, weight, etc., of the animal to be treated (see below).

To treat a animal, a diketopiperazine of formula I, or a pharmaceutically-acceptable salt or prodrug thereof, is administered to the animal. Preferably, the animal is a mammal, such as a rabbit, goat, dog, cat, horse or human. Effective dosage forms, modes of administration and dosage amounts for the compounds of the invention may be determined empirically, and making such determinations is within the skill of the art. It is understood by those skilled in the art that the dosage amount will vary with the particular compound(s) employed, the disease or condition to be treated, the severity of the disease or condition, the route(s) of administration, the rate of excretion of the compound, the duration of the treatment, the identity of any other drugs being administered to the animal, the age, size and species of the animal, and like factors known in the medical and veterinary arts. In general, a suitable daily dose of a compound of the present invention will be that amount of the compound which is the lowest dose effective to produce a therapeutic effect. However, the daily dosage will be determined by an attending physician or veterinarian within the scope of sound medical judgment. If desired, the effective daily dose may be administered as two, three, four, five, six or more sub-doses, administered separately at appropriate intervals throughout the day. Administration of the compound should be continued until an acceptable response is achieved.

The compounds of the present invention (i.e., diketopiperazines of formula I and pharmaceutically-acceptable salts and prodrugs thereof) may be administered to an animal patient for therapy by any suitable route of administration, including orally, nasally, rectally, vaginally, parenterally (e.g., intravenously, intraspinally, intraperitoneally, subcutaneously, or intramuscularly), intracisternally, transdermally, intracranially, intracerebrally, and topically (including buccally and sublingually). The preferred routes of administration are orally and topically.

While it is possible for a compound of the present invention to be administered alone, it is preferable to administer the compound as a pharmaceutical formulation (composition). The pharmaceutical compositions of the invention comprise a compound or compounds of the invention as the active ingredient(s) in admixture with one or more pharmaceutically-acceptable carriers and, optionally, with one or more other drugs. Each carrier must be "acceptable" in the sense of being compatible with the other ingredients of the formulation and not injurious to the animal. Pharmaceutically-acceptable carriers are well known in the art. Regardless of the route of administration selected, the compounds of the present invention are formulated into pharmaceutically-acceptable dosage forms by conventional methods known to those of skill in the art. See, e.g., *Remington's Pharmaceutical Sciences*.

Formulations of the invention suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of a compound or compounds of the present invention as an active ingredient. A compound or compounds of the present invention may also be administered as bolus, electuary or paste.

In solid dosage forms of the invention for oral administration (capsules, tablets, pills, dragees, powders, granules and the like), the active ingredient (i.e., one or more diketopiperazines of formula I and/or pharmaceutically-acceptable salts and/or prodrugs thereof) is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that releases the active ingredient only, or preferentially, in a certain portion of the gastrointestinal tract, optionally, in a delayed manner. Examples of embedding compositions which can be used include polymeric substances and waxes. The active ingredient can also be in microencapsulated form.

Liquid dosage forms for oral administration of the compounds of the invention include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active ingredient, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or salicylate, and which is solid at room temperature, but liquid at body temperature and, therefore, will melt in the rectum or vaginal cavity and release the active compound. Formulations of the present invention which are suitable for vaginal administration also include pessaries, tampons, creams, gels, pastes, foams or spray formulations containing such carriers as are known in the art to be appropriate.

Dosage forms for the topical or transdermal administration of compounds of the invention include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required.

The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane.

Transdermal patches have the added advantage of providing controlled delivery of compounds of the invention to the body. Such dosage forms can be made by dissolving, dispersing or otherwise incorporating one or more compounds of the invention in a proper medium, such as an elastomeric matrix material. Absorption enhancers can also be used to increase the flux of the compound across the skin. The rate of such flux can be controlled by either providing a rate-controlling membrane or dispersing the compound in a polymer matrix or gel.

Pharmaceutical formulations include those suitable for administration by inhalation or insufflation or for nasal or intraocular administration. For administration to the upper (nasal) or lower respiratory tract by inhalation, the compounds of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more compounds of the invention and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler.

For intranasal administration, compounds of the invention may be administered by means of nose drops or a liquid spray, such as by means of a plastic bottle atomizer or metered-dose inhaler. Liquid sprays are conveniently delivered from pressurized packs. Typical of atomizers are the Mistometer (Wintrop) and Medihaler (Riker).

Drops, such as eye drops or nose drops, may be formulated with an aqueous or nonaqueous base also comprising one or more dispersing agents, solubilizing agents or suspending agents. Drops can be delivered by means of a simple eye dropper-capped bottle or by means of a plastic bottle adapted to deliver liquid contents dropwise by means of a specially shaped closure.

Pharmaceutical compositions of this invention suitable for parenteral administrations comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue. The injectable materials can be sterilized for example, by filtration through a bacterial-retaining filter.

The formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The diketopiperazines of formula I, or a pharmaceutically-acceptable salt or prodrug thereof, may be given alone to treat a disease or condition according to the invention. Alternatively, the diketopiperazines of formula I, or a pharmaceutically-acceptable salt or prodrug thereof, may be given in combination with one or more other treatments or drugs suitable for treating the disease or condition. The compounds of the present invention can be administered prior to, in conjunction with (including simultaneously with) or after, the other treatment or drug.

For instance, when used to treat cancer, the compounds of the present invention can be administered prior to, in conjunction with or after, another anti-cancer treatment. Such anti-cancer treatments include surgery, radiation or chemotherapy using any of a variety of anti-cancer agents. Typically, any anti-cancer agent that has activity versus a susceptible tumor being treated may be administered prior to, in conjunction with or after, a diketopiperazine, or a pharmaceutically-acceptable salt or prodrug thereof, in the treatment of cancer according to the present invention. Examples of such agents can be found in Devita and Hellman (editors), *Cancer Principles and Practice of Oncology*, 6$^{th}$ edition, Feb. 15, 2001, Lippincott Williams & Wilkins (publishers), U.S. Pub. Patent Appl. No. 2008/0009507, PCT Application No. WO 2009/009793 and PCT Application No. WO 2009/032651, the complete disclosures of all of which are incorporated herein by reference as disclosing exemplary anti-cancer agents to be administered with diketopiperazine in methods of the present invention. A person of ordinary skill in the art would be able to discern which combinations of agents would be useful based on the particular characteristics of the drugs and the cancer involved. Typical anti-cancer agents useful in the present invention include anti-microtubule agents, anti-mitotic agents, platinum coordination complexes, alkylating agents, antibiotic agents, antimetabolites, hormones and hormonal analogs, topoisomerase I inhibitors, topoisomerase II inhibitors, angiogenesis inhibitors, signal transduction pathway inhibitors, proapoptotic agents and immunotherapeutic agents.

Anti-microtubule or anti-mitotic agents are phase specific agents active against the microtubules of tumor cells during M or the mitosis phase of the cell cycle. Examples of such agents include diterpenoids (e.g., paclitaxel and docetaxel) and vinca alkaloids (e.g., vinblastine, vincristine and vinorelbine).

Platinum coordination complexes are non-phase specific anti-cancer agents which are interactive with DNA. The platinum complexes enter tumor cells, undergo aquation and form intra- and interstrand crosslinks with DNA causing adverse biological effects to the tumor. Examples of platinum coordination complexes include cisplatin and carboplatin.

Alkylating agents are non-phase anti-cancer specific agents and strong electrophiles. Typically, alkylating agents form covalent linkages, by alkylation, to DNA through nucleophilic moieties of the DNA molecules such as phosphate, amino, sulfhydryl, hydroxyl, carboxyl and imidazole groups. Such alkylation disrupts nucleic acid function leading to cell death. Examples of alkylating agents include nitrogen mustards (e.g., cyclophosphamide, melphalan and chlorambucil), alkyl sulfonates (e.g, busulfan), nitrosoureas (e.g, carmustine), triazenes (e.g., dacarbazine) and imidazotetrazines (e.g., temozolomide).

Antibiotic anti-cancer agents are non-phase specific agents which bind or intercalate with DNA. Typically, such action results in stable DNA complexes or strand breakage, which disrupts ordinary function of the nucleic acids leading to cell death. Examples of antibiotic anti-cancer agents include actinomycins (e.g., dactinomycin), anthrocyclins (e.g., daunorubicin and doxorubicin) and bleomycins.

Topoisomerase I inhibitors include camptothecin and camptothecin derivatives (e.g, irinotecan, topotecan and the various optical forms of 7-(4-methylpiperazino-methylene)-10,11-ethylenedioxy-20-camptothecin). Camptothecins' cytotoxic activity is believed to be related to its topoisomerase I inhibitor activity Topoisomerase II inhibitors include epipodophyllotoxins (e.g., etoposide and teniposide). Epipodophyllotoxins are phase specific anti-cancer agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows.

Antimetabolite anti-cancer agents are phase specific agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-cancer agents include fluorouracil, methotrexate, cytarabine, mercaptopurine, thioguanine, hydroxyurea and gemcitabine.

Hormones or hormonal analogs are useful compounds for treating cancers in which there is a relationship between the hormone(s) and growth or lack of growth of the cancer. Examples of hormones and hormonal analogs useful in cancer treatment include adrenocorticosteroids (e.g., prednisone and prednisolone), aminoglutethimide and other aromatase inhibitors (e.g., anastrozole, letrazole, vorazole and exemestane), progestins (e.g., megestrol acetate), estrogens, androgens and anti-androgens (e.g., flutamide, nilutamide, bicalutamide, cyproterone acetate and 5α-reductases, such as finasteride and dutasteride), anti-estrogens (e.g., tamoxifen, toremifene, raloxifene, droloxifene, iodoxyfene and selective estrogen receptor modulators), gonadotropin-releasing hormone and analogs thereof which stimulate the release of leutinizing hormone and/or follicle stimulating hormone (e.g., goserelin aceteate and luprolide).

Angiogenesis inhibitors include anti-VEGF antibodies, inhibitors of integrin alpha$_v$beta$_3$, endostatin, angiostatin, danazol and those methylphenidate derivatives described in U.S. Pub. Patent Appl. No. 20060189655, particularly α-[phenyl-4-phenyl]-2-piperidineacetic acid methyl ester and α-[phenyl-4-phenoxy]-2-piperidineacetic acid methyl ester (i.e., those derivatives of methylphenidate (α-phenyl-2-piperidineacetic acid methyl ester) having the hydrogen of the phenyl group at the 4 (para) position replaced with phenyl or phenoxy).

Signal transduction pathway inhibitors are those inhibitors which block or inhibit a chemical process which evokes an intracellular change, particularly cell proliferation or differentiation. Signal transduction inhibitors useful in the present invention include inhibitors of receptor tyrosine kinases, non-receptor tyrosine kinases, serine/threonine kinases, PI3Ks, myoinositol signaling and Ras oncogenes, and SH2/SH3 domain blockers. Suitable inhibitors are described in PCT Application No. WO 2009/032651 and the references cited therein, and include kinase inhibitors, receptor antagonists, antibodies, ribozymes and anti-sense oligonucleotides. Specific examples include N-{3-chloro-4-[(3-fluorobenzyl)oxy]phenyl}6-[5-({[2-(methanesulfonyl)ethyl]amino}methyl)-2-furyl]-4-quinazolinamine (also known as lapatanib and Tykerb), inhibitors of farnesyltransferase, geranyl-geranyl transferase and CAAX proteases, Imclone C225 EGFR specific antibody, Herceptin (trastuzamab), erbB2 antibody, 2CB VEGFR2 specific antibody, BAY-43-9006, CI-1040, PD-098059, Wyeth CCI 779, and LY294002 and cell cycle signaling inhibitors (e.g., inhibitors of cyclin-dependent kinases).

Proapoptotic agents include Genta's G3139 bcl-2 antisense oligonucleotide which downregulates the expression of bcl-2 in tumors and tumor necrosis factor-related apoptosis-inducing ligand (TRAIL).

Immunotherapeutic agents include Imclone C225 EGFR specific antibody, Herceptin (trastuzamab), alemtuzumab, Erbitux (cetuximab), Avastin (bevacizumab), gemtuzumab, iodine 131 tositumomab, rituximab, erbB2 antibody, 2CB VEGFR2 specific antibody, anti-VEGF antibodies, and vaccines.

When used to treat a viral infection, the compounds of the present invention can be administered prior to, in conjunction with or after, another anti-viral drug. Anti-viral drugs include amantadine, rimantadine, pleconaril, lamivudine, fomivirsen, rifampicin, zidovudine, Relenza (zanamivir), Tamiflu (oseltamivir phosphate), Zovirax (acyclovir), interferons and antibodies.

The following Examples are intended to illustrate embodiments of the invention and are not intended to limit the invention.

EXAMPLES

Example 1

Synthesis of biphenyl-4-yl-(3,6-dioxo-piperazin-2-yl)-acetic acid methyl ester (Cpd. 5)

Biphenyl-4-yl-(3,6-dioxo-piperazin-2-yl)-acetic acid methyl ester (Cpd. 5) was synthesized as described below and illustrated in FIG. 1.

(A) Synthesis of biphenyl-4-yl-acetic Acid Methyl Ester (Cpd. 1)

To a stirred solution of 4-biphenylacetic acid (from Aldrich, 196487) (2 g., 9.4 mmol) in methanol (50 mL) at 0° C. was added drop-wise, thionylchloride (from Aldrich, 230464) (4.1 mL, 56.5 mmol), and the reaction was stirred for 0.5 hours at room temperature. The reaction mixture was concentrated in vacuo and the residue partitioned between ethylacetate (100 mL) and water (100 mL). The organic extract was washed with sodium bicarbonate (saturated solution, 100 mL), brine (saturated solution, 100 mL) and dried over magnesium sulphate. The solvents were removed in vacuo to afford Cpd. 1 as a yellow oil (2.1 g, ~100% yield). $^1$HNMR (CDCl$_3$) δH, 3.67, 2H (s, CH$_2$), 3.71, 3H (s, CH$_3$), 7.31-7.37, 3H (m, Ar—H), 7.40-7.45, 2H (m, Ar—H), 7.52-7.59, 4H (m, Ar—H); LCMS analysis (solvent MeCN/H$_2$O/0.1% HCO$_2$H, 5-95% gradient/H$_2$O 2.5 min, 95% 1.5 min., Phenomenex C18 reverse phase, flow rate 1 mL/min.) HPLC retention time 2.39 min.; mass found 167 (M-CO$_2$Me).

(B) Synthesis of biphenyl-4-yl-bromo-acetic Acid Methyl Ester (Cpd. 2)

To a stirred solution of biphenyl-4-yl-acetic acid methyl ester (5 g., 22.1 mmol) in carbon tetrachloride (from Acros, 16772) (25 mL) was added N-bromosuccinimide (from Aldrich, 18350) (3.9 g., 22.1 mmol) and benzoyl peroxide (from Acros, 21178) (0.54 g, 2.2 mmol) and the reaction was heated to reflux for 48 hours. The reaction mixture was cooled to room temperature, filtered and the filtrate concentrated in vacuo to afford Cpd. 2 as a crude yellow oil (6.24 g., 93% yield). $^1$HNMR (CDCl$_3$) δH, 3.81, 3H (s, CH$_3$), 5.41, 1H (s, Br—CH), 7.33-7.39, 2H (m, Ar—H), 7.41-7.46, 3H (m, Ar—H), 7.54-7.63, 4H (m, Ar—H); LCMS analysis (solvent MeCN/H$_2$O/0.1% HCO$_2$H, 5-95% gradient/H$_2$O 2.5 min, 95% 4 min., Phenomenex C18 reverse phase, flow rate 1 mL/min.) HPLC retention time 4.39 min.

(C) Synthesis of 2-amino-3-biphenyl-4-yl-succinic Acid (Cpd. 3)

To a stirred solution of diethylacetamido malonate (from Fisher, 11393) (0.53 mg., 12.5 mmol) in ethanol (10 mL) at 0° C., was added drop-wise to a solution of sodium ethoxide (from Fluka, 71212) (0.7 mL, 2% solution in ethanol) and the reaction was stirred at room temperature for 0.5 hours. A solution of biphenyl-4-yl-bromo-acetic acid methyl ester (0.5 g, 1.6 mmol) in ethanol (5 mL) was added drop-wise and the reaction stirred at room temperature for a further 1.5 hours. The reaction was quenched by the addition of water (25 mL) and extracted with ethylacetate (3×50 mL). The organic extracts were combined, dried over magnesium sulphate and concentrated in vacuo to afford a crude residue. The crude residue was purified using flash chromatography (SiO$_2$) eluting with ethylacetate and isohexane (1:1) to afford 2-acetylamino-3-biphenyl-4-yl-2-ethoxycarbonyl-succinic acid 1-ethyl ester 4-ethyl ester as a pale yellow solid (0.49 g, 68% yield) (contains ~10% of the corresponding 4-methyl ester). $^1$HNMR (CDCl$_3$) δH(ppm); 1.2, 3H (t, CH$_3$ J=7.02 Hz), 1.22, 3H (t, CH$_3$ J=7.02 Hz), 1.3, 3H (t, CH$_3$ J=7.02 Hz), 1.9, 3H (s, CH$_3$), 4.04-4.23, 4H (m, 2×CH$_2$), 4.31, 2H (q, CH$_2$ J=7.02 & 14.3 Hz), 5.01, 1H (s, CH), 6.5, 1H (br s, NH), 7.31-7.36, 1H (m, Ar—H), 7.40-7.46, 4H (m, Ar—H), 7.5-7.54, 2H (m, Ar—H), 7.56-7.60, 2H (m, Ar—H); LCMS analysis (solvent MeCN/H$_2$O/0.1% HCO$_2$H, 5-95% gradient/H$_2$O 2.5 min, 95% 4 min., Phenomenex C18 reverse phase, flow rate 1 mL/min.) HPLC retention times 4.68 and 4.9 min. (diastereoisomers); mass found 465 (M+H).

A solution of 2-acetylamino-3-biphenyl-4-yl-2-ethoxycarbonyl-succinic acid 1-ethyl ester 4-ethyl ester (0.33 g., 0.76 mmol) in 9N hydrochloric acid (10 mL) was heated at reflux for 7 hours. The reaction mixture was cooled to room temperature and concentrated in vacuo to afford Cpd. 3 as a white crystalline solid (0.21 g., 96% yield). $^1$HNMR (DMSO-d$_6$) δH(ppm); 4.24, 1H (d, CH J=7.02 Hz), 4.38, 0.5H (d, CH J=7.02 Hz), 4.44, 0.5H (d, CH J=7.02 Hz), 7.33-7.39, 2H (m, Ar—H), 7.40-7.48, 3H (m, Ar—H), 7.62-7.69, 4H (m, Ar—H), 8.4, 3H (br s, NH$_3^+$) (diastereoisomers); LCMS analysis (solvent MeCN/H$_2$O/0.1% HCO$_2$H, 5-95% gradient/H$_2$O 2.5 min, 95% 4 min., Phenomenex C18 reverse phase, flow rate 1 mL/min.) HPLC retention time 5.9 min.; mass found 286 (M+H).

(D) Synthesis of 2-amino-3-biphenyl-4-yl-succinic Acid Dimethyl Ester hydrochloride (Cpd. 4)

To a stirred solution of 2-amino-3-biphenyl-4-yl-succinic acid hydrochloride (1.54 g., 48 mmol) in methanol (100 mL) at 0° C. was added dropwise to thionyl chloride (4.2 mL, 57.5 mmol) and the reaction was heated at 40° C. for 29 hours. The reaction mixture was concentrated in vacuo and the residue partitioned between saturated sodium bicarbonate (100 mL) and ethylacetate (100 mL). The aqueous layer was washed with ethyl acetate (2×50 mL) and the organics combined, dried over magnesium sulphate and concentrated in vacuo to afford the free base as a pale yellow oil. The residue was dissolved in methanol (50 mL) and an excess solution of HCl (4N solution in dioxane) (from Aldrich, 345547) (2 mL) added. The resulting solution was concentrated to dryness and the solid recrystallized from ethylacetate/diethyl ether (1:1) to afford Cpd. 4 as a pale yellow solid (0.37 g., 24% yield). $^1$HNMR (DMSO-d$_6$) δH(ppm); 3.52, 2.7H (s, CH$_3$), 3.67, 0.3H (s, CH$_3$), 3.71, 2.7H (s, CH$_3$), 3.75, 0.3H (s, CH$_3$), 4.48, 0.8H (d, CH J=7.6 Hz), 4.53, 0.2H (d, CH J=6.7 Hz), 4.57-4.63, 1H (m, CH), 7.3-7.41, 3H (m, Ar—H), 7.44-7.51, 2H (m, Ar—H), 7.64-7.72, 4H (m, Ar—H), 8.9, 3H (br s, NH$_3^+$) (diastereoisomers); LCMS analysis (solvent MeCN/H$_2$O/0.1% HCO$_2$H, 5-95% gradient/H$_2$O 2.5 min, 95% 6 min., Phenomenex C18 reverse phase, flow rate 1 mL/min.) HPLC retention time 6.05 min.; mass found 314 (M+H).

(E) Synthesis of biphenyl-4-yl-(3,6-dioxo-piperazin-2-yl)-acetic Acid Methyl Ester (Cpd. 5)

A solution of Fmoc-Gly-OH (from Bachem) (1.66 g., 5.6 mmol), N—(3-dimethylaminopropyl)-N'-ethylcarbodiimide (from Aldrich, 39391) (1.1 g., 5.7 mmol), 1-hydroxybenzotriazole (from Aldrich, 54804) (0.76 g., 5.6 mmol) and triethylamine (0.4 mL, 2.8 mmol) in dimethylformamide (50 mL) was stirred at room temperature for 1 hour. A solution of 2-amino-3-biphenyl-4-yl-succinic acid dimethyl ester hydrochloride (0.98 g., 2.8 mmol) in dimethylformamide (10 mL) was added and the reaction mixture was stirred at room temperature for a further 14 hours. The solvent was removed in vacuo and the residue partitioned between ethylacetate (100 mL) and sodium bicarbonate (100 mL, saturated solution in water). The aqueous layer was washed with ethylacetate (2×100 mL), the organics combined, dried over magnesium sulphate and concentrated in vacuo to afford a crude residue. The crude product was purified using flash chromatography (SiO$_2$) eluting with ethylacetate/isohexane (3:1) to afford 2-biphenyl-4-yl-3-[2-(9H-fluoren-9-ylmethoxycarbonylamino)-acetylamino]-succinic acid dimethyl ester as a white crystalline solid (0.89 g., 54% yield). $^1$HNMR (CDCl$_3$) δH(ppm); 3.71-3.73 (m, 7H), 3.81 0.2H (d, CH J=5.6 Hz), 3.86, 0.3H (d, CH J=5.8 Hz), 3.9, 0.3H (d, CH J=5.3 Hz), 3.94, 0.2H (d, CH J=5.8 Hz), 4.13-4.24 (m, 1H), 4.28-4.44 (m, 2.5H), 4.5 (d, 0.5H J=4.4 Hz), 5.1-5.4 (m, 2H), 6.4 (d, NH J=8.5 Hz), 7.19 (d, NH J=9.4 Hz), 7.23-7.34, 5H (m, Ar—H), 7.35-7.42, 4H (m, Ar—H), 7.47-7.60, 6H (m, Ar—H), 7.74, 2H (d, Ar—H J=7.6 Hz); LCMS analysis (solvent MeCN/H$_2$O/0.1% HCO$_2$H, 5-95% gradient/H$_2$O 2.5 min, 95% 4 min., Phenomenex C18 reverse phase, flow rate 1 mL/min.) HPLC retention times 5.33 and 5.47 min. (diastereoisomers).; mass found 593 (M+H).

2-Biphenyl-4-yl-3-[2-(9H-fluoren-9-ylmethoxycarbonylamino)-acetylamino]-succinic acid dimethyl ester (0.86 g., 1.5 mmol) was dissolved in a solution of 20% piperidine-dimethylformamide (30 mL) and the reaction mixture was stirred at room temperature for 2 hours and then at 60° C. for 4 hours. The reaction mixture was concentrated in vacuo and the crude material was triturated using diethyl ether and then filtered to afford an off-white solid. The solid material was triturated using ethylacetate and the isolated product washed with methanol, filtered and dried under vacuum to afford Cpd. 5 as an off-white crystalline solid (0.26 g., 52% yield). $^1$HNMR (DMSO-d$_6$) δH(ppm); 2.83, 1H (d, CH$_2$ $_J$=17.2 Hz), 3.38, 0.7H (dd, CH$_2$ J=2.9 & 17.2 Hz), 3.47, 0.3H (dd, CH$_2$ J=2.6 & 17.5 Hz), 3.65, 3H (s, CH$_3$), 4.16, 0.3H (d, CH J=5.6 Hz), 4.27, 0.7H (d, CH J=4.7 Hz), 4.43-4.46, 0.3H (m, CH), 4.5-4.53, 0.7H (m, CH), 7.3-7.37, 3H (m, Ar—H), 7.41-7.46, 2H (m, Ar—H), 7.59-7.68, 4H (m, Ar—H), 7.97-8.14, 2H (2×NH) (diastereoisomers); LCMS analysis (solvent 0.1% HCO$_2$H/MeCN, H$_2$O/ 0.1% HCO$_2$H, 7.5-95% gradient/H$_2$O 11 min, Thermo Betabasic 100×4.6 mm C18 reverse phase, flow rate 1 mL/min.) HPLC retention time 5.61 min.; mass found 339 (M+H).

Example 2

Inhibition of Proliferation of Cancer Cells

Assays were performed to determine the effect of Cpd. 5 (synthesis described in Example 1) on proliferation of two cancer cell lines. These two cell lines were STTG grade 4 astrocytoma cell line and AU565 breast cancer cell line. Both cell lines were obtained from American Type Culture Collection, Rockville, Md. (ATCC).

To perform the assays, a 50 mM stock solution of Cpd. 5 was prepared in DMSO and frozen at −80° C. Aliquots of the stock solution were removed and 100 µM dilutions were made in Iscove's modified Dulbecco's medium (IMDM; obtained from ATCC) supplemented with 10% fetal bovine serum (FBS) and penicillin/streptomycin solution. Controls containing equivalent amounts of DMSO to the 100 µM solution were mixed for comparative purposes. 100 µl of the resulting solutions were then added to 96 well culture plates in triplicate and placed in a 37° C. incubator with 5% CO$_2$ to warm. The controls were the PI3 kinase inhibitor, LY294002, and an inactive PI3 kinase inhibitor related compound, LY303511 (both obtained from Sigma).

At this point, cells were removed from passage flasks using trypsin and counted using trypan blue to establish cell counts/ml and viability. For all experiments, viability of cells was greater than 95%. Solutions of 4,000 cells/100 µl were prepared in the medium from above and 100 µl of the solutions were added to each well of the plates. The plates were placed back in the incubator and incubated with the compounds for 96 hours.

Following incubation, cell proliferation was assayed by adding 20 µl Promega cell titer aqueous one reagent to each well. Promega cell titer reagent is a solution containing a tetrazolium dye that is reduced by living cells to a formazan dye, and this reduction is proportional to the number of living cells present in the well. The plates were incubated at 37° C. for an additional 4-18 hours to allow the colorimetric assay to develop, and the OD of each well was determined in a microplate reader using a 530 nm filter. The OD of wells containing cell titer reagent in culture medium with no cells was subtracted from the OD of all experimental readings.

The % decrease of the total cell titer signal was determined using the following formula. ((Diluent OD−Experimental OD)/Diluent OD))×100. Data are presented in Table 1 as mean % decrease of cell titer signal of three separate experiments, plus or minus standard deviation. In the mean % decrease column, a positive number means a decrease in cell titer signal, while a negative number means an increase in cell titer signal. The p values were calculated versus diluent controls.

TABLE 1

| | | Mean % Decrease | | |
|---|---|---|---|---|
| COMPOUND | CELLS | MEAN % DECREASE | STD. DEVIATION | P VALUE |
| CPD. 5 (50 µM) | STTG | 78.74 | 3.93 | 0.000 |
| LY294002 (20 µM) | STTG | −46.72 | 24.13 | 0.014 |
| LY303511 (20 µM) | STTG | −4.74 | 6 | 0.121 |
| CPD. 5 (50 µM) | AU565 | 13.44 | 6.36 | 0.011 |
| LY294002 (20 µM) | AU565 | 61.95 | 6.58 | 0.000 |
| LY303511 (20 µM) | AU565 | −2.34 | 3.02 | 0.125 |

To determine whether the decrease in cell titer signal caused by Cpd. 5 was due to the inhibition of proliferation or to cytotoxicity, STTG and AU565 cells were seeded at 10,000 cells/well in 96-well plates and grown until a confluent monolayer was obtained. Under these conditions, the cells should no longer proliferate. The culture medium was IMDM supplemented with 10% FBS. After the cells reached confluence, the culture medium was removed by aspiration and replaced with fresh medium containing the test compounds (see Table 2 below). The cell cultures were incubated for an additional 24 hours in the presence of the added compounds and then the cell titer signal was assayed by adding 20 µl Promega cell titer aqueous one reagent to each well. The plates were incubated at 37° C. for an additional 2 hours to allow the colorimetric assay to develop, and the OD of each well was determined in a microplate reader using a 530 nm filter. The OD of wells containing cell titer reagent in culture medium with no cells was subtracted from the OD of all experimental readings. The results of triplicate experiments are presented in Table 2.

The % decrease of the total cell titer signal was determined using the following formula. ((Diluent OD−Experimental OD)/Diluent OD))×100. Data are presented in Table 2 as mean % decrease of cell titer signal of three separate experiments, plus or minus standard deviation. In the mean % decrease column, a positive number means a decrease in cell titer signal, while a negative number means an increase. The p values were calculated versus diluent controls.

This experiment was repeated, except using incubations of 18 hours, instead of 24 hours, in the presence of the compounds and 4 hours, instead of 2 hours, for color development. The results are presented in Table 3 below.

The combined results of the experiments show that the majority of the decrease in cell titer signal caused by Cpd. 5 was due to inhibition of proliferation and not to cytotoxicity.

TABLE 2

Mean % Decrease

| COMPOUND | CELLS | MEAN % DECREASE | STD. DEVIATION | P VALUE |
|---|---|---|---|---|
| CPD. 5 (10 μM) | AU565 | −8.87 | 9.53 | 0.091 |
| CPD. 5 (50 μM) | AU565 | −10.79 | 11.32 | 0.087 |
| CPD. 5 (100 μM) | AU565 | −11.05 | 1.58 | 0.000 |
| LY294002 (50 μM) | AU565 | 2.94 | 25.74 | 0.426 |
| 70% Methanol* | AU565 | 100.19 | 3.45 | 0.000 |
| CPD. 5 (10 μM) | STTG | −7.13 | 20.93 | 0.293 |
| CPD. 5 (50 μM) | STTG | −1.76 | 21.08 | 0.446 |
| CPD. 5 (100 μM) | STTG | −10.79 | 26.38 | 0.259 |
| LY294002 (50 μM) | STTG | 26.12 | 13.10 | 0.013 |
| 70% Methanol* | STTG | 103.85 | 6.69 | 0.000 |

*Added 5 minutes prior to cell titer reagent.

TABLE 3

Mean % Decrease

| COMPOUND | CELLS | MEAN % DECREASE | p VALUE |
|---|---|---|---|
| CPD. 5 (10 μM) | AU565 | −5.61 | 0.283 |
| CPD. 5 (50 μM) | AU565 | −9.73 | 0.052 |
| CPD. 5 (100 μM) | AU565 | −10.69 | 0.038 |
| LY294002 (50 μM) | AU565 | 22.25 | 0.004 |
| 70% Methanol* | AU565 | 98.03 | 0.000 |
| CPD. 5 (10 μM) | STTG | 0.81 | 0.313 |
| CPD. 5 (50 μM) | STTG | 21.25 | 0.000 |
| CPD. 5 (100 μM) | STTG | 18.96 | 0.028 |
| LY294002 (50 μM) | STTG | 26.27 | 0.001 |
| 70% Methanol* | STTG | 99.16 | 0.000 |

*Added 5 minutes prior to cell titer reagent.

Example 3

Inhibition of MMP-9

As a result of their ability to cleave components of the extracellular matrix (ECM) and remodel the cellular microenvironment, matrix metalloproteinases (MMPs) are thought to play a role in the development and progression of tumors. Thiennu H. Vu and Zena Werb, "Gelatinase B: Structure, Regulation, and Function," pages 115-148, in *Matrix Metalloproteinases* (Academic Press, Editors William C. Parks and Robert P. Mecham, 1998). The type IV collagenases, in particular, have been implicated in tumor invasion and metastasis due to their ability to degrade basement membrane collagens. Id. Matrix metalloproteinase-9 (MMP-9) (also known as gelatinase B) is widely thought to be a type IV collagenase. Id. MMP-9, while not commonly expressed in normal cells, has been found to be expressed in tumors from diverse sites, including skin, lungs, breast, colorectum, liver, prostate, brain, bone marrow and bone. Id. In some tumors, MMP-9 is expressed by the tumor cells themselves. Id. In other cases, other cells surrounding or found in the tumors express MMP-9. Id. In many tumors, high expression of MMP-9 correlates with tumor invasiveness and metastatic potential. Id.

Assays were performed to determine the effect of Cpd. 5 (synthesis described in Example 1) on the secretion of MMP-9 by the BT001 glioma cell line. The BT001 cell line was established as follows from cells obtained after surgery. The excised tissue was treated briefly with a protease cocktail, and the resulting cell suspension was cultured in IMDM supplemented with 10% FBS. Expanded cells were then frozen for future use.

A fresh 50 mM stock solution of Cpd. 5 was prepared in ethanol and warmed to 37° C. Aliquots of the stock solution were removed and diluted in IMDM supplemented with 0.1% FBS, insulin-transferrin-sodium selenite (ITSS) solution, and penicillin/streptomycin solution to prepare experimental culture media (final concentrations of Cpd. 5 ranged from 10-100 μM). Ethanol in the culture medium was used as diluent control.

The BT001 cells were cultured in 25 $cm^2$ flasks in IMDM containing 10% FBS at 37° C. and 5% $CO_2$. When cells reach 70-80% confluence, they were washed two times with IMDM that had been warmed to 37° C. in a water bath. The experimental culture media containing Cpd. 5 were then added to the flasks (4.5 ml per flask), and the flasks were incubated at 37° C. and 5% $CO_2$ for 48 hours. The conditioned media were then removed from the cells, and cellular debris was removed by centrifugation at 2000 rpm for 10 minutes. The supernatants were then transferred to sterile tubes and stored at −20° C.

Gelatin zymograms were used to evaluate MMP release and activity in the samples. Precast 10% polyacrylamide gels impregnated with gelatin were obtained from Invitrogen, Carlsbad, Calif. Ten μL of each of the thawed conditioned media were mixed with an equal volume of SDS-PAGE loading dye without reducing agent (obtained from Invitrogen, Carlsbad, Calif.), applied to the gels and separated at 150 volts for 1 hour. The gels were then processed following the manufacturer's recommended protocol (includes renaturing the gels for one hour and incubating overnight at 37° C. with gentle shaking for protease digestion of gelatin). Visualization of MMP activity was done by staining the gel with Invitrogen Simple Safe blue commassie solution and photographing the gel on a Kodak Image station. The intensity of the bands in the photos was determined using bundled Kodak software. Percent decrease was determined with the following formula:

$$(\text{Intensity of diluent control}) - (\text{Intensity of treatment})/(\text{Intensity of diluent control}) \times 100.$$

The results are presented below in Table 4. The data presented in Table 4 are the means of three or four replicate experiments.

TABLE 4

| | | Mean % Decrease | | | |
|---|---|---|---|---|---|
| COMPOUND | CELLS | MEAN % DECREASE PRO-MMP-9 | P VALUE (VERSUS DILUENT CONTROL) | MEAN % DECREASE ACTIVE MMP-9 | P VALUE (VERSUS DILUENT CONTROL) |
| Cpd. 5 (10 μM) | BT001 | 6.89 ± 20.51 | 0.297 | 49.55 ± 21.49 | 0.008 |
| Cpd. 5 (50 μM) | BT001 | 36.13 ± 20.53 | 0.019 | 40.51 ± 9.73 | 0.002 |
| Cpd. 5 (100 μM) | BT001 | 45.55 ± 20.50 | 0.297 | 71.08 ± 17.47 | 0.001 |

The same experiment as described above for BT001 cells was performed using STTG astrocytoma cells (for a description of the STTG cell line, see Example 2). It was found that Cpd. 5 had no effect on the release of MMP-9 from the STTG cells (data not shown).

A similar experiment as described above for BT001 cells was performed using primary human microglial cells (isolated from a lobectomy from an epileptic patient). It was found that 100 μM Cpd. 5 inhibited the release of active MMP-9 from the primary microglial cells by 35.89% (using supernatants that had been concentrated 10×). Cpd. 5 did not inhibit the release of pro-MMP-9 from the primary microglial cells (using supernatants that had been concentrated 10×; data not shown).

Example 4

Inhibition of Proliferation of Cancer Cells

Assays were performed to determine the effect of Cpd. 5 on proliferation of an additional cancer cell line. This cell line was the U-118 metastatic astrocytoma cell line. It was obtained from ATCC.

To perform the assays, a 50 mM stock solution of Cpd. 5 was prepared in DMSO and frozen at −80° C. Aliquots of the stock solution were removed and dilutions containing from 50 μM to 300 μM Cpd. 5 were made in Iscove's modified Dulbecco's medium (IMDM; obtained from ATCC) supplemented with 10% fetal bovine serum (FBS) and penicillin/streptomycin solution. Controls containing equivalent amounts of DMSO to the 300 μM solution were mixed for comparative purposes. 100 μl of the resulting solutions were then added to 96 well culture plates in triplicate and placed in a 37° C. incubator with 5% $CO_2$ to warm. The controls included the PI3 kinase inhibitor, LY294002, and an inactive PI3 kinase inhibitor related compound, LY303511 (both obtained from Sigma).

Cells were removed from passage flasks using trypsin and ethylenediaminetetracetic acid (EDTA) and counted using trypan blue to establish cell counts/ml and viability. For all experiments, viability of cells was greater than 95%. Solutions of 4,000 cells/100 μl were prepared in the medium from above, and 100 μl of the solutions were added to each well of the plates. The plates were placed back in the incubator and incubated with the compounds for 96 hours.

Following incubation, cell proliferation was assayed by adding 20 μl Promega cell titer aqueous one reagent to each well. Promega cell titer reagent is a solution containing a tetrazolium dye that is reduced by living cells to a formazan dye, and this reduction is proportional to the number of living cells present in the well. The plates were incubated at 37° C. for an additional 4 hours to allow the colorimetric assay to develop, and the OD of each well was determined in a microplate reader using a 530 nm filter. The OD of wells containing cell titer reagent in culture medium with no cells was subtracted from the OD of all experimental readings. The results are presented in Table 5 below.

The % decrease of the total cell titer signal was determined using the following formula. ((Diluent OD−Experimental OD)/Diluent OD)×100. Data are presented in Table 5 as mean % decrease of cell titer signal of three separate experiments, plus or minus standard deviation. In the mean % decrease column, a positive number means a decrease in cell titer signal, while a negative number means an increase in cell titer signal. The p values were calculated versus diluent controls.

TABLE 5

| | Mean % Decrease | |
|---|---|---|
| COMPOUND (Final Concentration) | CELLS | MEAN % DECREASE |
| CPD. 5 (150 μM) | U-118 | 65.84 |
| CPD. 5 (100 μM) | U-118 | 25.93 |
| CPD. 5 (75 μM) | U-118 | 4.11 |
| CPD. 5 (50 μM) | U-118 | −7.82 |
| CPD. 5 (37.5 μM) | U-118 | −46.50 |
| CPD. 5 (25 μM) | U-118 | −50.62 |
| LY294002 (20 μM) | U-118 | 19.75 |
| LY303511 (20 μM) | U-118 | −25.93 |

The above experiment was repeated using the U-118 cells at 3000 cells/well. The results are shown in Table 6 below.

TABLE 6

| | Mean % Decrease | | |
|---|---|---|---|
| COMPOUND (Final Concentration) | CELLS | MEAN % DECREASE | P VALUE |
| CPD. 5 (150 μM) | U-118 | 59.70 | 0.003 |
| CPD. 5 (100 μM) | U-118 | 20.51 | 0.108 |
| CPD. 5 (75 μM) | U-118 | −3.05 | 0.404 |
| CPD. 5 (50 μM) | U-118 | −15.63 | 0.177 |
| CPD. 5 (37.5 μM) | U-118 | −25.28 | 0.062 |

TABLE 6-continued

Mean % Decrease

| COMPOUND (Final Concentration) | CELLS | MEAN % DECREASE | P VALUE |
|---|---|---|---|
| CPD. 5 (25 µM) | U-118 | −25.28 | 0.087 |
| LY294002 (40 µM) | U-118 | 86.04 | 0.001 |
| LY303511 (40 µM) | U-118 | 0.41 | 0.490 |

Example 5

Effects of Cpd. 5 on HUVECs

Assays were performed to determine the effect of Cpd. 5 on proliferation of human umbilical vein endothelial cells (HUVECs). Passage 4-5 HUVECs, human source lot number 13047 (obtained from Lonza) were put into the wells of a 96-well tissue culture plate at 1200 cells/well in 100 µl endothelial growth medium-2 (EGM-2) complete medium (obtained from Lonza). A 50 mM stock solution of Cpd. 5 was prepared in DMSO and frozen at −80° C. Aliquots of the stock solution were removed and dilutions containing from 50 µM to 300 µM Cpd. 5 were made in EGM-2 complete medium (Lonza). Controls containing equivalent amounts of DMSO to the 200 µM solution were mixed for comparative purposes. 100 µl of the resulting solutions were then added to the cells in the 96-well culture plates in triplicate and placed in a 37° C. incubator with 5% $CO_2$ for 72 hours. The controls were the PI3 kinase inhibitor, LY294002, and an inactive PI3 kinase inhibitor related compound, LY303511 (both obtained from Sigma).

Following incubation, cell proliferation was assayed by adding 20 µl Promega cell titer aqueous one reagent to each well. Promega cell titer reagent is a solution containing a tetrazolium dye that is reduced by living cells to a formazan dye, and this reduction is proportional to the number of living cells present in the well. The plates were incubated at 37° C. for an additional 4 hours to allow the colorimetric assay to develop, and the OD of each well was determined in a microplate reader using a 530 nm filter. The OD of wells containing cell titer reagent in culture medium with no cells was subtracted from the OD of all experimental readings.

The % decrease of the total cell titer signal was determined using the following formula. ((Diluent OD−Experimental OD)/Diluent OD)×100. Data are presented in Table 7 as mean % decrease of cell titer signal of three separate experiments, plus or minus standard deviation. In the mean % decrease column, a positive number means a decrease in cell titer signal, while a negative number means an increase in cell titer signal. The p values were calculated versus diluent controls. The results are presented in Table 7 below.

As shown in Table 7, Cpd. 5 at 100 µM final concentration inhibited the proliferation of HUVECs. At lower concentrations, it appeared to stimulate proliferation of HUVECs. The reason for this stimulation is not known, but may be due to the DMSO in which Cpd. 5 is dissolved.

TABLE 7

Mean % Decrease

| COMPOUND | MEAN % DECREASE | STD. DEVIATION | P VALUE |
|---|---|---|---|
| CPD. 5 (25 µM) | −48.60 | 20.79 | 0.040 |
| CPD. 5 (50 µM) | −14.44 | 17.99 | 0.234 |
| CPD. 5 (100 µM) | 62.04 | 1.54 | 0.000 |

When endothelial cells are cultured on extracellular matrix protein gels in the presence of angiogenic signals, they arrange themselves into structures loosely resembling capillary blood vessels ("tube formation"). Cpd. 5 was tested for its ability to affect tube formation and was found to have no observable effect at 50 µM or 100 µM.

Example 6

Inhibition of Akt Phosphorylation in Breast Cancer Cells

Assays were performed to determine the effect of Cpd. 5 (synthesis described in Example 1) on phosphorylation of Akt in the AU565 breast cancer cell line. Akt (or protein kinase B, PKB) is a serine/threonine kinase that promotes cellular survival. Akt is activated in response to many different growth factors, including IGF-1, EGF, bFGF, insulin, interleukin-3 (IL-3), IL-6, heregulin and VEGF. Akt has three isoforms, and activation of all three isoforms is similar in that phosphorylation of two sites is necessary for full activity. Once activated, Akt exerts anti-apoptotic effects through phosphorylation of substrates that directly or indirectly regulate apoptosis. Activation of the phosphatidylinositol 3 kinase (PI3K)/Akt signaling pathway contributes to tumorigenesis in many types of tissues, including breast, ovarian, brain, prostate and lymph tissues. It has been found that Akt is constitutively active in an array of cancers and contributes to both chemotherapeutic resistance and radiation resistance.

AU565 cells were grown in 75 $cm^2$ flasks using Iscove's modified Dulbecco's medium (IMDM; obtained from Lonza) supplemented with 10% fetal bovine serum (FBS, HyClone) and 1% penicillin/streptomycin solution (Lonza). Cells were removed from the flasks using trypsin/EDTA (Lonza) and counted using trypan blue to establish cell counts. Cells in the above supplemented IMDM medium were added to the wells of a 96-well plate (20,000 cells/well), and the plates were incubated at 37° C., 5% $CO_2$, for 24 hours. After 24 hours, the medium was removed and replaced with medium not containing any serum (serum-free IMDM), and the plates were incubated at 37° C., 5% $CO_2$, for an additional 24 hours.

After this incubation, the test compounds were added to the plates as follows. A 20 mM stock solution of Cpd. 5 was prepared in DMSO and frozen at −80° C. Aliquots of the stock solution were removed and dilutions were made in serum-free IMDM medium. Controls containing equivalent amounts of DMSO (0.05% and 0.25%) were mixed for comparative purposes. The other control was the PI3 kinase inhibitor, LY294002 (obtained from Sigma). 100 µl of each test compound solution were then added to 96 well culture plates in duplicate, and the plates were placed back into the incubator and incubated at 37° C., 5% $CO_2$, for 1 hour.

Following this incubation, 100 µl of serum-free IMDM containing either 0 or 400 ng/ml insulin-like growth factor-1 (IGF-1) (obtained from Sigma), an Akt phosphorylation promoter, were added, and the plates incubated at 37° C., 5% $CO_2$, for 1 more hour. At the end of this time, the cells were fixed immediately with 4% formaldehyde, refrigerated, and the extent of phosphorylation of Akt determined using the Akt Cellular Activation of Signaling ELISA (CASE™ Kit for AKT 5473; SABiosciences, Frederick, Md.) following the manufacturer's protocols. The CASE™ Kit for AKT S473 quantifies the amount of activated (phosphorylated) Akt protein relative to total Akt protein in parallel assays using a conventional ELISA format with colorimetric detection. The Akt phosphorylation site is serine 473 and is recognized by one of the antibodies used in the one of the two parallel assays to provide the measure of activated Akt protein. The other antibody used in the other parallel assay recognizes Akt to provide the measure of total Akt protein. Both primary antibodies are detected using a horseradish peroxidase-labeled secondary antibody. Addition of the manufacturer's Developing Solution for 10 minutes, followed by addition of the manufacturer's Stop Solution, produces the product which can be measured colorimetrically.

The results were calculated as follows. The treatment groups containing IGF-I/DMSO were subtracted from their respective IGF-1/DMSO only groups (positive control). This value was divided by the difference between the respective DMSO only group (negative control) and the respective positive control. This value represents the percent inhibition of Akt phosphorylation attributable to the inhibitor alone since the contribution of DMSO is subtracted out.

The results are presented in Table 8. As can be seen from Table 8, Cpd. 5 completely inhibited phosphorylation of Akt.

TABLE 8

Mean % Inhibition

| TREATMENT | MEAN % INHIBITION OF Akt PHOSPHORYLATION | STD. DEVIATION | P VALUE |
|---|---|---|---|
| CPD. 5 (10 µM) | 104.0 | 21.4 | 0.038 |
| CPD. 5 (50 µM) | 92.0 | 26.7 | 0.044 |
| LY294002 (50 µM) | 92.4 | 30.5 | 0.035 |

Example 7

Inhibition of Akt Phosphorylation in Melanoma Cells

Assays were performed to determine the effect of Cpd. 5 (synthesis described in Example 1) on phosphorylation of Akt in WM-266-4, a metastatic melanoma cell line obtained from ATCC. The WM-266-4 cells were grown in 25 $cm^2$ flasks using IMDM medium (obtained from Lonza) supplemented with 10% fetal bovine serum (FBS, HyClone) and 1% penicillin/streptomycin solution (Lonza). Cells were removed from the flasks using trypsin/EDTA (Lonza) and counted using trypan blue to establish cell counts. Cells in the above supplemented IMDM medium were added to the wells of a 96-well plate (10,000 cells/well), and the plates were incubated at 37° C., 5% $CO_2$, for 24 hours. After 24 hours, the medium was removed and replaced with medium not containing any serum (serum-free IMDM), and the plates were incubated at 37° C., 5% $CO_2$, for an additional 24 hours.

After this incubation, the test compounds were added to the plates as follows. A 20 mM stock solution of Cpd. 5 was prepared in DMSO and frozen at −80° C. Aliquots of the stock solution were removed and dilutions were made in serum-free IMDM medium. Final concentrations of Cpd. 5 were 10 µM and 50 µM. Controls containing equivalent amounts of DMSO as the two concentrations of Cpd. 5 (0.05% and 0.25%) were mixed for comparative purposes. The other control was the PI3 kinase inhibitor, LY294002 (obtained from Sigma), final concentration of 50 µM. 100 µl of each test compound solution were then added to 96 well culture plates in duplicate, and the plates were placed back into the incubator and incubated at 37° C., 5% $CO_2$, for 1 hour.

Following this incubation, 100 µl of serum-free IMDM containing either 0 or 400 ng/ml IGF-1 (obtained from Sigma), an Akt phosphorylation promoter, were added, and the plates incubated at 37° C., 5% $CO_2$, for 1 more hour. At the end of this time, the cells were fixed immediately with 4% formaldehyde, refrigerated, and the extent of phosphorylation of Akt determined using the Akt Cellular Activation of Signaling ELISA (CASE™ Kit for AKT S473; SABiosciences, Frederick, Md.) following the manufacturer's protocols. The CASE™ Kit for AKT S473 quantifies the amount of activated (phosphorylated) Akt protein relative to total Akt protein. For further details of the CASE ELISA assay, see Example 6.

The results were calculated as follows. The treatment groups containing IGF-I/DMSO were subtracted from their respective IGF-1/DMSO only groups (positive control). This value was divided by the difference between the respective DMSO only group (negative control) and the respective positive control. This value represents the percent inhibition of Akt phosphorylation attributable to the inhibitor alone since the contribution of DMSO is subtracted out.

The results are presented in Table 9 below. As shown there, Cpd. 5 at 10 µM gave 101.8% inhibition and at 50 µM gave 47% inhibition of Akt phosphorylation, as compared to 23.1% inhibition for 50 µM LY294002, the known PI3 kinase inhibitor. It should also be noted that, in a separate experiment, Cpd. 5 did not inhibit the proliferation of WM-266-4 cells, whereas LY294002 did inhibit proliferation of these cells (by 105%).

TABLE 9

Mean % Inhibition

| TREATMENT | MEAN % INHIBITION OF Akt PHOSPHORYLATION | STD. DEVIATION | P VALUE |
|---|---|---|---|
| CPD. 5 (10 µM) | 101.8 | 3.9 | 0.026 |
| CPD. 5 (50 µM) | 55.9 | 21.7 | 0.036 |
| LY294002 (50 µM) | 23.1 | 21.2 | 0.309 |

In the WM-266-4 melanoma cell line there are two proliferation pathways—one through Akt kinase and one through MAP kinase (MAPK). See Russo et al., *Int. J. Oncol.*, 34(6):1481-1489 (June 2009) (abstract, PMID 19424565, full article in process) (in melanoma, both the MAPK and PI3K/Akt pathways are constitutively activated through multiple mechanisms). Both kinases are dependent on PI3 kinase, which would explain why LY294002 inhibited proliferation of these cells, whereas Cpd. 5 did not, although both compounds inhibited Akt phosphorylation. Even though Cpd. 5 did not inhibit proliferation of the WM-266-4 cell line, the inhibition of Akt phosphorylation (activation) by Cpd. 5 should make the WM-266-4 cells more sensitive to standard anti-cancer therapies (e.g, chemotherapy and radiation). See Sinnberg et al., *J. Invest. Dermatol., PMID* 19078992, abstract of article Epub Dec. 11, 2008 (inhibition of the PI3K/Akt pathway potently increases the sensitivity of melanoma cells to chemotherapy).

I claim:

1. A method of inhibiting the activation of Akt by cells comprising contacting the cells with an effective amount of a diketopiperazine, wherein the diketopiperazine is biphenyl-4-yl-(3,6-dioxo-piperazin-2-yl)-acetic acid methyl ester.

2. The method of claim 1 wherein the contacting takes place in vivo.

* * * * *